(12) United States Patent
Nakaso

(10) Patent No.: US 8,113,063 B2
(45) Date of Patent: Feb. 14, 2012

(54) FLUID MEASUREMENT DEVICE, METHOD OF MEASURING FLUID, AND FLUID SPACIAL DISTRIBUTION VISUALIZATION DEVICE

(75) Inventor: Noritaka Nakaso, Tokyo (JP)

(73) Assignee: Toppan Printing Co., Ltd., Tokyo (JP)

( * ) Notice: Subject to any disclaimer, the term of this patent is extended or adjusted under 35 U.S.C. 154(b) by 0 days.

(21) Appl. No.: 12/929,804

(22) Filed: Feb. 16, 2011

(65) Prior Publication Data

US 2011/0138904 A1    Jun. 16, 2011

Related U.S. Application Data

(63) Continuation of application No. PCT/JP2009/063820, filed on Aug. 4, 2009.

(30) Foreign Application Priority Data

Aug. 19, 2008    (JP) ................................. 2008-210832

(51) Int. Cl.
G01F 1/00    (2006.01)

(52) U.S. Cl. ........................................................ 73/861
(58) Field of Classification Search ................... None
See application file for complete search history.

(56) References Cited

U.S. PATENT DOCUMENTS

| | | | |
|---|---|---|---|
| 4,557,142 A * | 12/1985 | Hensley et al. ............. | 73/152.19 |
| 2009/0229344 A1 * | 9/2009 | Nakaso ........................ | 73/24.01 |

FOREIGN PATENT DOCUMENTS

| | | |
|---|---|---|
| JP | 11-66465 | 3/1999 |
| JP | 2006-300743 | 11/2006 |
| WO | 2004/086028 A1 | 10/2004 |

OTHER PUBLICATIONS

Naoya Iwata et al., "Analysis of Ball Surface Acoustic Wave Sensor Response to Wide Variety of Gases Using Gas Chromatography," IEICE Technical Report US2007-47, The Institute of Electronics, Information and Communication Engineers, Sep. 2007, p. 25-30.
International Search Report for PCT/JP2009/063820 mailed on Oct. 6, 2009.
Takamichi Nakamoto, et al., "Odor Sensing System", Institute of Electronics, Information, and Communication Engineers, C-1, vol. J82-C-1, No. 4, pp. 156-164, Apr. 1999.
Hiroshi Ishida, et al., "Improvement of Olfactory Video Camera: Gas/Odor Flow Visualization System", Department of Physical Electronics, Tokyo Institute of Technology, Sensors and Actuators B 82, (2002), pp. 256-261.

* cited by examiner

Primary Examiner — Harshad Patel

(57) ABSTRACT

A fluid measurement device includes a fluid measurement unit which includes a plurality of fluid measurement sections configured to measure a measurement fluid introduced into a measurement chamber from the outside, each of the fluid measurement sections including a fluid measurement sensor on which the measurement fluid introduced into the measurement chamber acts. The fluid measurement devise includes a measurement controller which sequentially introduces the measurement fluid into each of the fluid measurement sections every set time shorter than a fluid measurement time required for one of the fluid measurement sections to conduct one fluid measurement, the measurement controller measuring the fluid to provide a time difference for each of the fluid measurement sections, and a central controller which accumulates fluid measurement data from the fluid measurement sensors and rapidly measures a change of the external measurement fluid.

17 Claims, 15 Drawing Sheets

FLUID MEASUREMENT DEVICE, METHOD OF MEASURING FLUID, AND FLUID SPACIAL DISTRIBUTION VISUALIZATION DEVICE

CROSS-REFERENCE TO RELATED APPLICATIONS

This is a Continuation Application of PCT Application No. PCT/JP2009/063820, filed Aug. 4, 2009, which was published under PCT Article 21(2) in Japanese.

This application is based upon and claims the benefit of priority from prior Japanese Patent Application No. 2008-210832, filed Aug. 19, 2008, the entire contents of which are incorporated herein by reference.

BACKGROUND OF THE INVENTION

1. Field of the Invention

The present invention relates to a fluid measurement device which measures the characteristics of a fluid, a method of measuring a fluid, and a fluid spacial distribution visualization device using the fluid measurement device.

2. Description of the Related Art

Recently, a fuel cell which directly extracts electricity from a hydrogen gas has been under development. As hydrogen is a gas that easily leaks, plumbing equipment which carries hydrogen is required to be highly secure. There is also a need for techniques which detect the leakage of hydrogen and identify the place of the leakage.

A fluid spacial distribution visualization device is disclosed in Nonpatent document 1 ("Improvement of olfactory video camera: gas/odor flow visualization system" by Hiroshi Ishida, Takafumi Tokuhiro, Takamichi Nakamoto and Toyosaka Morizumi, Sensors and Actuators B 83, 2002, p. 256-p. 261). This fluid spacial distribution visualization device visualizes the odor of a gas to identify the source of the gas. In this fluid spacial distribution visualization device, a sensitive film is formed on the surface of an AT-cut quartz oscillator. Thus, a resonance frequency that changes in response to the gas acting on the sensitive film is measured by using QCM gas sensors. The QCM gas sensors are one-dimensionally or two-dimensionally arranged at intervals of several cm. Measurement results of the concentrations of the gas obtained by the respective QCM gas sensors are displayed on a display screen in the form of moving images. Spacial movements of the unevenness of the gas concentrations are observed so that the movement of the gas is visualized.

A method is disclosed in Patent document 2 ("Odor sensing system" published in the journal of the Institute of Electronics, Information and Communication Engineers C-1 by Takamichi Nakamoto and Toyosaka Morizumi, April, 1994, Vol. J82-C-I, No. 4, pp. 156-pp. 164). According to this method, an odor is identified or a gas concentration is calculated from the responses of a plurality of sensor elements by, for example, a neural net computing circuit or principal component analysis. The respective sensor elements include sensitive films having gas response characteristics different from one another. Here, the odor is not exclusively the odor perceived by a human being, but the odor means a characteristic numerical value determined by the kind and amount of a gas independent from the chemical identification of the components and concentration of the gas. Outputs from the respective sensor elements including the sensitive films different in gas response characteristics from one another are measured, such that the concentration and kind of the gas are measured in a comprehensive manner. In some cases, a particular gas alone may be measured (highly selective measurement) by gas sensors including sensitive films which have the same gas response characteristics. However, it is rare that the particular gas alone is measured.

BRIEF SUMMARY OF THE INVENTION

According to one aspect of the invention, a fluid measurement device includes: a fluid measurement unit which includes a plurality of fluid measurement sections configured to measure a measurement fluid introduced into a measurement chamber from the outside, each of the fluid measurement sections including a fluid measurement sensor on which the measurement fluid introduced into the measurement chamber acts; a measurement controller which sequentially introduces the measurement fluid into each of the fluid measurement sections every set time shorter than a fluid measurement time required for one of the fluid measurement sections to conduct one fluid measurement, the measurement controller measuring the fluid to provide a time difference for each of the fluid measurement sections; and a central controller which accumulates fluid measurement data from the fluid measurement sensors and rapidly measures a change of the external measurement fluid.

According to one other aspect of the invention, a method of measuring a fluid, the method includes: measuring the fluid in a plurality of fluid measurement sections in which fluid measurement sensors are respectively disposed in measurement chambers, the measurement of the fluid being conducted by sequentially introducing the measurement fluid into each of the fluid measurement sections every set time shorter than a fluid measurement time required for one of the fluid measurement sections to conduct one fluid measurement and causing the measurement fluid to act on the fluid measurement sensors to provide a time difference for each of the fluid measurement sections; and accumulating fluid measurement data from the fluid measurement sensors and rapidly measuring a change of the external measurement fluid.

According to one other aspect of the invention, a fluid spacial distribution visualization device includes: a plurality of fluid measurement devices which respectively measure a change of a predetermined measurement fluid at different positions, each of the fluid measurement devices including a plurality of fluid measurement sections configured to measure the measurement fluid introduced into a measurement chamber from the outside, each of the fluid measurement sections including a fluid measurement sensor on which the measurement fluid introduced into the measurement chamber acts; a display unit which displays a distribution of the measurement fluid in a space of two or more dimensions on the basis of a measurement value of the measurement fluid measured by each of the fluid measurement devices; a measurement control unit which sequentially introduces the measurement fluid into each of the fluid measurement sections every set time shorter than a fluid measurement time required for one of the fluid measurement sections to conduct one fluid measurement in each of the fluid measurement devices, the measurement control unit measuring the fluid to provide a time difference for each of the fluid measurement sections in each of the fluid measurement devices; and a central control unit which accumulates fluid measurement data from the fluid measurement sensors in each of the fluid measurement devices and rapidly measures a change of the external measurement fluid in each of the fluid measurement devices, the central control unit including a visualizer configured to visualize and display, on the display unit, the change of the measurement fluid obtained from the fluid measurement data in each of the fluid measurement devices.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
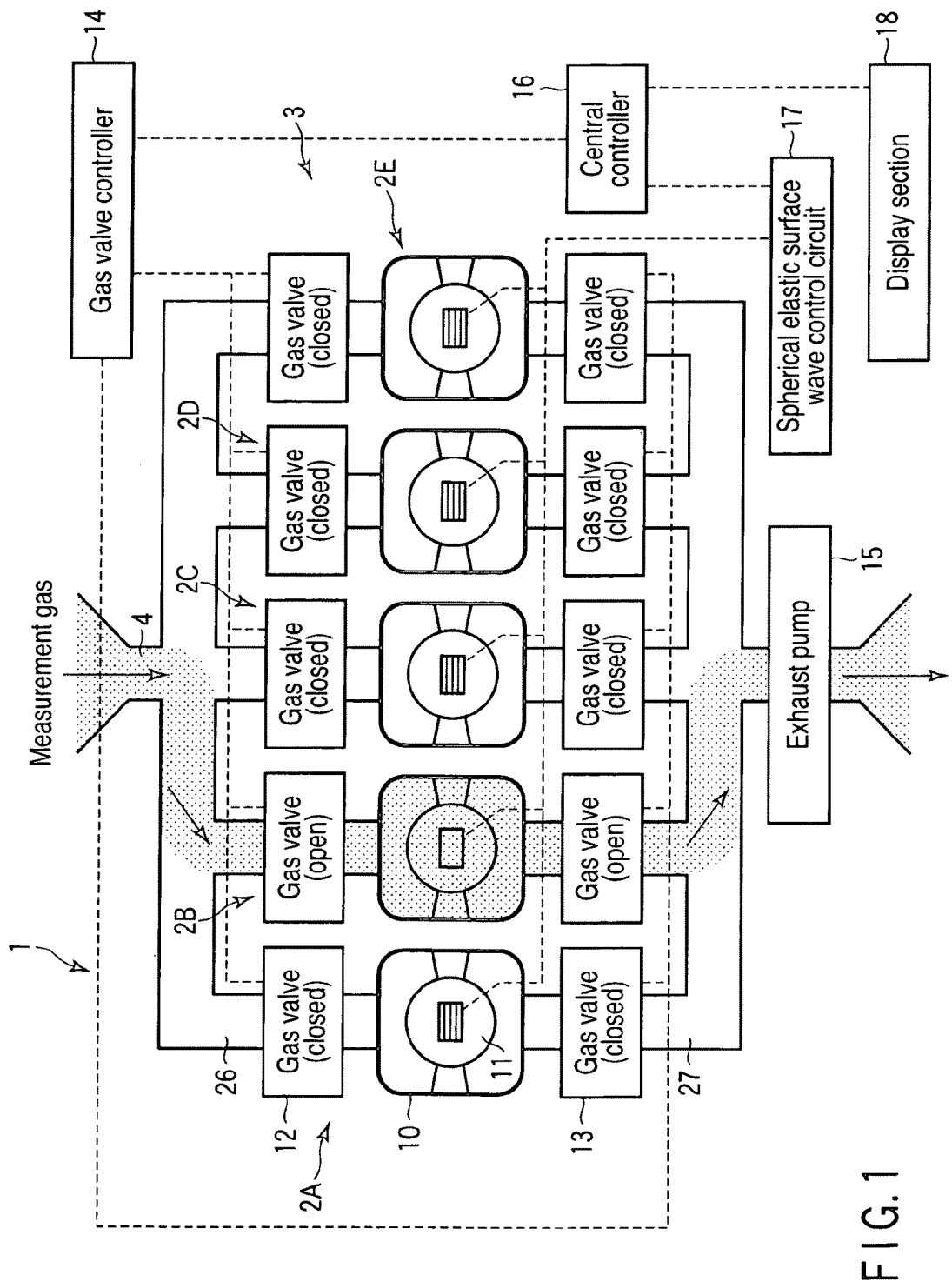
FIG. 1 is a schematic diagram showing the entire configuration of a fluid measurement device according to a first embodiment of the present invention.
Figure 2:
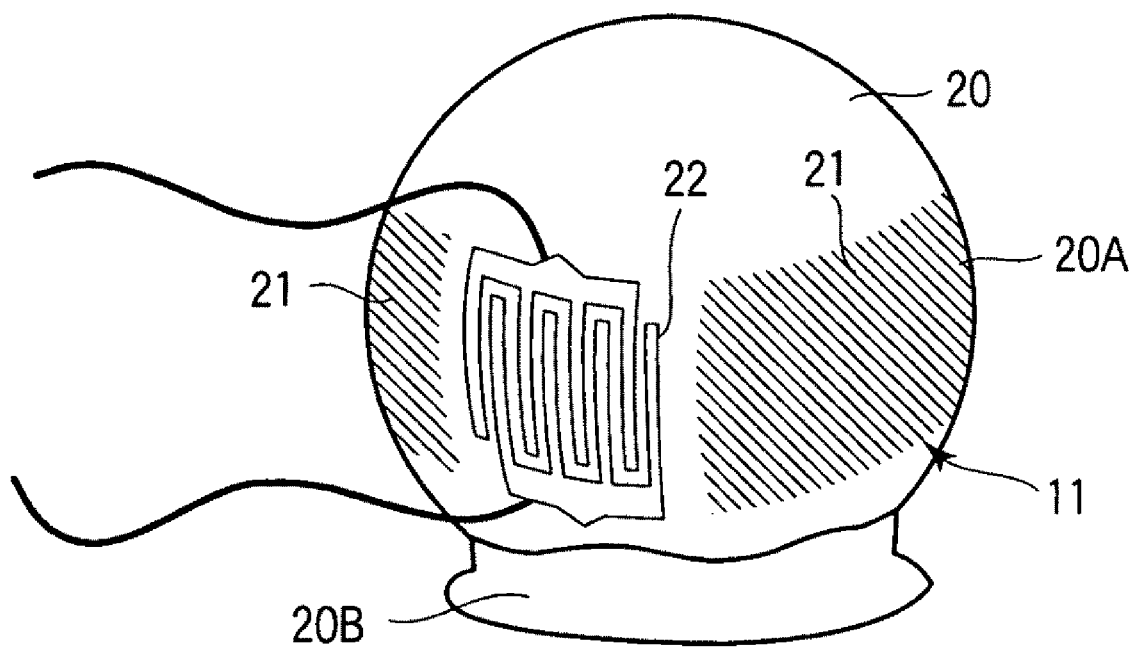
FIG. 2 is a front view showing the configuration of a gas measurement chamber of the fluid measurement device according to the first embodiment.

A fluid measurement device 1 according to a first embodiment of the present invention is described with reference to FIG. 1 to FIG. 3. FIG. 1 is a schematic diagram showing the configuration of the fluid measurement device 1 according to the first embodiment of the present invention. The fluid measurement device 1 according to the present embodiment includes a fluid measurement unit 3. The fluid measurement unit 3 includes a plurality of (five in the present embodiment) fluid measurement sections 2A to 2E.

The fluid measurement sections 2A to 2E have the same configuration. It should be noted that the configuration of the fluid measurement section 2A is only described below as an example and the same components of the other fluid measurement sections 2B to 2E are provided with the same reference numbers and are not described.

The fluid measurement section 2A includes a gas measurement chamber 10. A gas measurement sensor 11 which measures a gas as a specimen is provided in the gas measurement chamber 10. For example, a spherical elastic surface wave element sensor is used as the gas measurement sensor 11.

The fluid measurement section 2A also includes an inflow duct (inflow portion) 26 leading to the gas measurement chamber 10, and an outflow duct (outflow portion) 27 leading out of the gas measurement chamber 10. The inflow duct 26 is provided with an inflow gas valve (first valve) 12, and the outflow duct 27 is provided with an outflow gas valve (second valve) 13. The inflow gas valve 12 and the outflow gas valve 13 of each of the fluid measurement sections 2A to 2E are connected to a gas valve controller (measurement controller) 14. The gas valve controller 14 controls the opening/closing operation of the inflow gas valve 12 and the outflow gas valve 13 of each of the fluid measurement sections 2A to 2E.

The inflow duct 26 of each of the fluid measurement sections 2A to 2E is coupled to an introduction gas pipe 4 which introduces a measurement gas. The outflow duct 27 of each of the fluid measurement sections 2A to 2E is coupled to an exhaust pump 15. Thus, a gas in the outside air is taken into the gas measurement chamber 10 of each of the fluid measurement sections 2A to 2E by suction pressure from the exhaust pump 15.

The gas measurement sensor 11 of each of the fluid measurement sections 2A to 2E is connected to the spherical elastic surface wave control circuit 17. The gas valve controller 14 is connected to a central controller 16. The central controller 16 is connected to the spherical elastic surface wave control circuit 17 and a display 18. The spherical elastic surface wave control circuit 17 inputs a burst signal to the gas measurement sensor 11 of each of the fluid measurement sections 2A to 2E in accordance with a proper timing, described later. An output from the gas measurement sensor 11 of each of the fluid measurement sections 2A to 2E is measured in accordance with the proper timing. The measurement results are sequentially sent to the central controller 16 via the spherical elastic surface wave control circuit 17. The central controller 16 accumulates fluid measurement data from the gas measurement sensor 11 of each of the fluid measurement sections 2A to 2E, and thereby processes the measurement result sent from the gas measurement sensor 11 of each of the fluid measurement sections 2A to 2E as a time change. In this manner, a change of the external measurement gas is rapidly measured by the central controller 16. The measurement results processed by the central controller 16 are displayed on the display section 18.

Here, the spherical elastic surface wave element sensor used as the gas measurement sensor 11 is described with reference to FIG. 2. FIG. 2 is a diagram showing the configuration of the gas measurement chamber 10 of the fluid measurement section 2A of the fluid measurement device 1. It should be noted that the gas measurement chambers 10 of the other fluid measurement sections 2B to 2E have the same configuration and are not described.

The spherical elastic surface wave element sensor used as the gas measurement sensor 11 is formed by coating the surface of a spherical elastic surface wave element 20 having a diameter of about 1 mm or 3.3 mm with a sensitive film 20A of about 30 nm which is an alloy of palladium and nickel. The spherical elastic surface wave element 20 is fixed to the gas measurement chamber 10 by a fixing adhesive agent 20B. The spherical elastic surface wave element 20 is provided with at least one annularly continuous elastic surface wave revolution circuit 21 around which an elastic surface wave revolves. The elastic surface wave revolution circuit 21 is provided with an interdigital electrode 22 as an element that excites the elastic surface wave. A high-frequency burst voltage of about 150 MHz is applied to the interdigital electrode 22 from the spherical elastic surface wave control circuit 17. The voltage is applied to the interdigital electrode 22 in a burst form, such that the elastic surface wave is excited, and the elastic surface wave makes multiple revolutions along the elastic surface wave revolution circuit 21. The elastic surface wave which has revolved around the elastic surface wave revolution circuit 21 a specific number of times is received by the interdigital electrode 22, and output to the spherical elastic surface wave control circuit 17 as a voltage signal. As a result, the phase and strength of the output signal a predetermined time after the input of the burst signal are measured. The revolution velocity and damping factor of the elastic surface wave are found from the measurement results.

Here, the sensitive film 20A is an alloy of palladium and nickel, and its elastic properties change with the concentration of hydrogen within the gas measurement chamber 10. In response to the change of the elastic properties of the palladium-nickel alloy, the revolution velocity and damping factor of the elastic surface wave revolving around the elastic surface wave revolution circuit 21 of the spherical elastic surface wave element 20 change. Therefore, the concentration of hydrogen within the gas measurement chamber 10 is measured by finding the revolution velocity and damping factor of the elastic surface wave.

The material that constitutes the sensitive film 20A is not exclusively the palladium-nickel alloy that changes in its elastic properties with the concentration of hydrogen. That is, the sensitive film 20A has only to be made of a material that changes in its elastic properties in response to the action of a particular fluid.

Moreover, the gas measurement sensor 11 may be an electric resistance gas sensor. The electric resistance gas sensor includes a sensitive film, and this sensitive film is made of a material that adsorbs a particular fluid and thereby changes in its electric resistance. The electric resistance of the sensitive film is measured to measure the concentration of the particular fluid.

Alternatively, the gas measurement sensor 11 may be a field effect transistor type (FET type) gas sensor. The FET type gas sensor includes a sensitive film provided in a gate electrode portion of an FET and made of a material which selectively reacts with a particular fluid. The sensitive film adsorbs the particular fluid and thereby changes its work function. The threshold voltage and resistance change of the sensitive film are measured, such that the work function is found, and the concentration of the particular fluid is found.

Now, the action of the fluid measurement device 1 according to the present embodiment is described with reference to FIG. 3. FIG. 3 is a correlation diagram showing the operations of the fluid measurement sections 2A to 2E of the fluid measurement device 1.

Suppose that a gas is introduced into one of the five fluid measurement sections 2A to 2E, for example, the fluid measurement section 2B as shown in FIG. 1. When an external gas is introduced into the fluid measurement section 2B, the inflow gas valve 12 and the outflow gas valve 13 of the fluid measurement section 2B are opened. As a result, a suction force from the exhaust pump 15 acts on the gas measurement chamber 10 of the fluid measurement section 2B. Thus, a measurement fluid is introduced into the gas measurement chamber 10 of the fluid measurement section 2B from the introduction gas pipe 4 via the inflow gas valve 12. At the same time, in response to the introduction of the measurement fluid, an old gas within the gas measurement chamber 10 is discharged and exchanged for a new gas. When the gas exchange is completed, the inflow gas valve 12 and the outflow gas valve 13 of the fluid measurement section 2B are closed. The time of the gas exchange including the opening/closing time of the inflow gas valve 12 and the outflow gas valve 13 is about 0.1 seconds.

Furthermore, there is a wait for a proper set time while the inflow gas valve 12 and the outflow gas valve 13 of the fluid measurement section 2B are being closed. As a result, the introduced gas acts on the sensitive film of the gas measurement sensor 11. The above-mentioned set time is about 0.2 seconds for, for example, a hydrogen sensor in which a palladium-nickel alloy film of 30 nm is formed in the spherical elastic surface wave element 20 having a diameter of 3.3 mm.

After the above-mentioned set time since the closing of the inflow gas valve 12 and the outflow gas valve 13 of the fluid measurement section 2B, a first burst signal is input to the interdigital electrode 22 of the gas measurement sensor 11. Further, an elastic surface wave which has revolved around the elastic surface wave revolution circuit 21 a specific number of times is measured, and its phase and strength are analyzed.

The response characteristics of the burst signal are measured as many times as a preset number of times of averaging. Here, a time of about 1 ms is required for the influence of the previous elastic surface wave to disappear, so that second and following measurements are conducted 1 ms or more after the previous measurement. That is, the next burst signal is input 1 ms after the input of the previous burst signal. Further, measurements are conducted as many times as the predetermined number of times of averaging, and then averaged data is calculated. Here, if the number of times of averaging is 100, 0.1 seconds are required for the measurement time of the elastic surface wave.

Thus, a measurement time $t_0$ required for one gas measurement sensor 11 is as shown in Equation (1):

$$t_0 = t_1 + t_2 + t_3 = 2.2 \text{ seconds} \qquad (1)$$

wherein $t_1$ is the time of exchanging the gas within the gas measurement chamber 10 of the fluid measurement section 2B (including the opening/closing time of the inflow gas valve 12 and the outflow gas valve 13), $t_2$ is the time taken for the gas introduced into the gas measurement chamber 10 to complete its action on the sensitive film of the gas measurement sensor 11, and $t_3$ is the measurement time of the elastic surface wave.

Equation (1) also holds true with the gas measurement sensors 11 of the fluid measurement sections 2A and 2C to 2E other than the fluid measurement section 2B. Therefore, when a measurement is conducted by the gas measurement sensor 11 of one fluid measurement section 2B alone, a time resolution of the measurement is 2.2 seconds.

Figure 3:
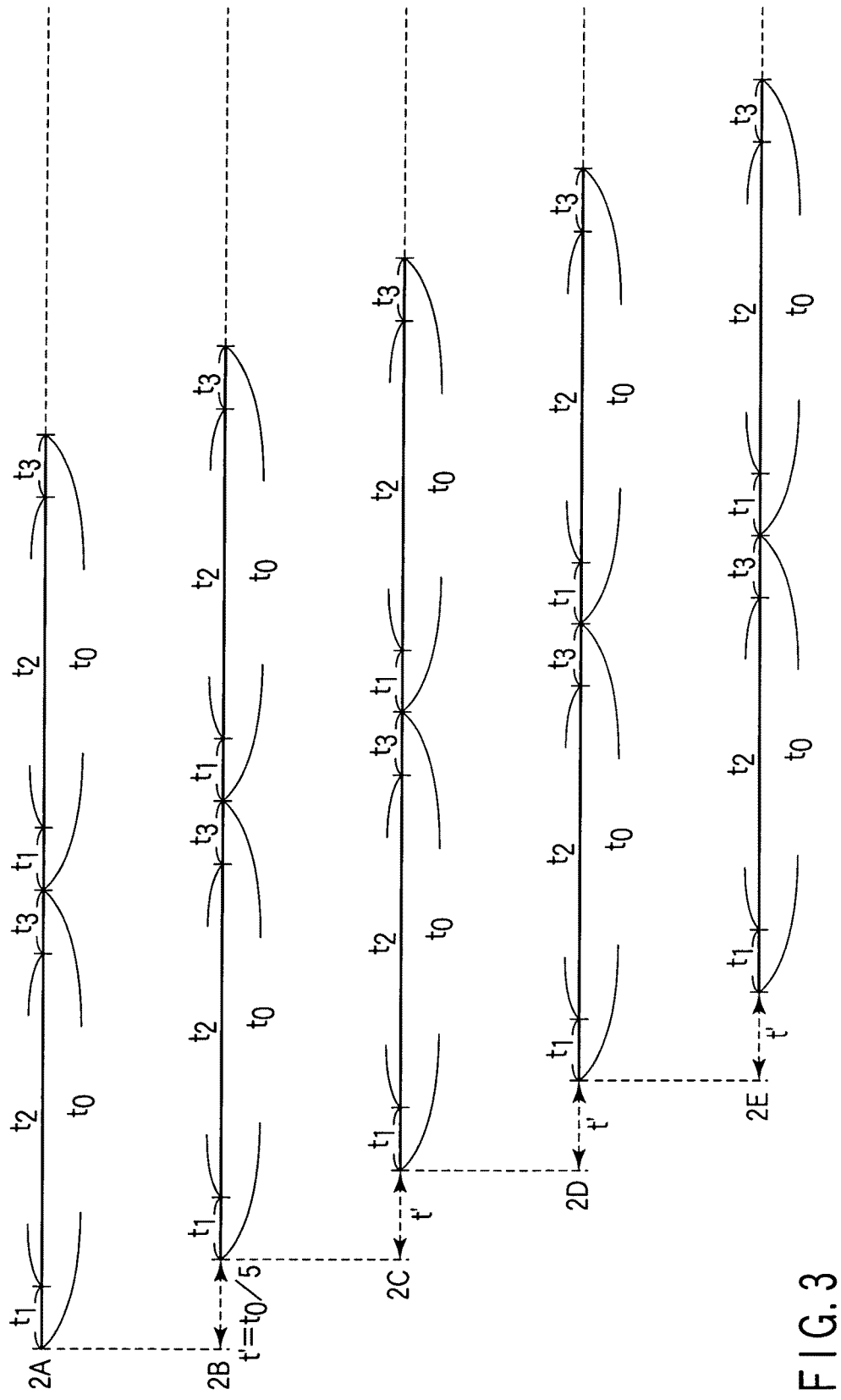
FIG. 3 is a schematic diagram illustrating the action of the fluid measurement device according to the first embodiment.

Furthermore, as shown in FIG. 3, in the present embodiment, the inflow gas valve 12 and the outflow gas valve 13 of the fluid measurement section 2C for the next measurement are opened $t_0/5$ after the opening of the inflow gas valve 12 and the outflow gas valve 13 of the fluid measurement section 2B. As a result, a gas measurement operation similar to that in the fluid measurement section 2B is performed in the gas measurement chamber 10 of the next fluid measurement section 2C $t_0/5$ behind the gas measurement chamber 10 of the fluid measurement section 2B.

Moreover, the inflow gas valve 12 and the outflow gas valve 13 of the fluid measurement section 2D for the next measurement are opened $t_0/5$ after the opening/closing of the inflow gas valve 12 and the outflow gas valve 13 of the fluid measurement section 2C. As a result, a gas measurement operation similar to that in the fluid measurement section 2C is performed in the gas measurement chamber 10 of the next fluid measurement section 2D $t_0/5$ behind the gas measurement chamber 10 of the fluid measurement section 2C.

That is, the gas measurement operations described above are sequentially performed in the gas measurement chambers 10 of the fluid measurement sections 2A to 2E at intervals of $t_0/5$. This time is 1/5 of the gas measurement time $t_0$ necessary for the gas measurement sensor 11 of each of the fluid measurement sections 2A to 2E. Thus, if $t_0$ is 2.2 seconds, a time resolution t' of the measurement by the fluid measurement device 1 according to the present embodiment is as shown in Equation (2)

$$t' = t_0 \div 5 = 0.44 \text{ seconds} \quad (2).$$

Therefore, the time resolution of the measurement by the fluid measurement device 1 is not limited by the measurement time $t_0$ necessary for one gas measurement sensor 11 of each of the fluid measurement sections 2A to 2E. That is, in the fluid measurement device 1, the operation of introducing a gas into the gas measurement chamber 10 of each of the fluid measurement sections 2A to 2E and measuring the gas is sequentially performed to provide a time difference at every set time which is shorter than a fluid measurement time required for one fluid measurement by the gas measurement sensor 11 of each of the fluid measurement sections 2A to 2E. At the same time, the respective fluid measurement sections 2A to 2E wait in parallel for the time in which the introduced gas acts on the sensitive film of the gas measurement sensor 11. Thus, the time resolution of the measurement by the fluid measurement device 1 can be increased without being limited by the gas measurement time $t_0$ necessary for one gas measurement sensor 11 of each of the fluid measurement sections 2A to 2E. If the number of the fluid measurement sections 2A to 2E each of which includes one gas measurement sensor 11 is increased, a measurement is conducted with a higher time resolution.

Accordingly, the fluid measurement device 1 having the configuration described above has the following effects. That is, in the fluid measurement device 1 according to the present embodiment, the operation of introducing a gas into the gas measurement chamber 10 of each of the fluid measurement sections 2A to 2E is sequentially performed to provide a time difference at every set time which is shorter than the fluid measurement time $t_0$ required for one fluid measurement by the gas measurement sensor 11 of each of the fluid measurement sections 2A to 2E. As a result, the respective fluid measurement sections 2A to 2E wait in parallel for the time in which the introduced gas acts on the sensitive film of the gas measurement sensor 11. Thus, the time resolution of the measurement by the fluid measurement device 1 can be increased without being limited by the gas measurement time $t_0$ necessary for one gas measurement sensor 11 of each of the fluid measurement sections 2A to 2E. Consequently, changes in the composition and constitution of a gas can be detected with a high time resolution.

In each of the fluid measurement sections 2A to 2E according to the first embodiment, the inflow duct 26 is provided with the inflow gas valve 12, and the outflow duct 27 is provided with the outflow gas valve 13. However, the present invention is not limited to this. That is, a gas valve (12, 13) which opens/closes the path of a fluid has only to be provided in at least one of the inflow duct 26 and the outflow duct 27.

Second Embodiment

Now, a fluid measurement device 25 according to a second embodiment is described with reference to FIG. 4. In the present embodiment, the fluid measurement device 25 obtained by modifying the configuration of the fluid measurement device 1 according to the first embodiment in the following manner is provided. It should be noted that the same parts as those in the first embodiment are provided with the same reference numbers and are not described.

Figure 4:
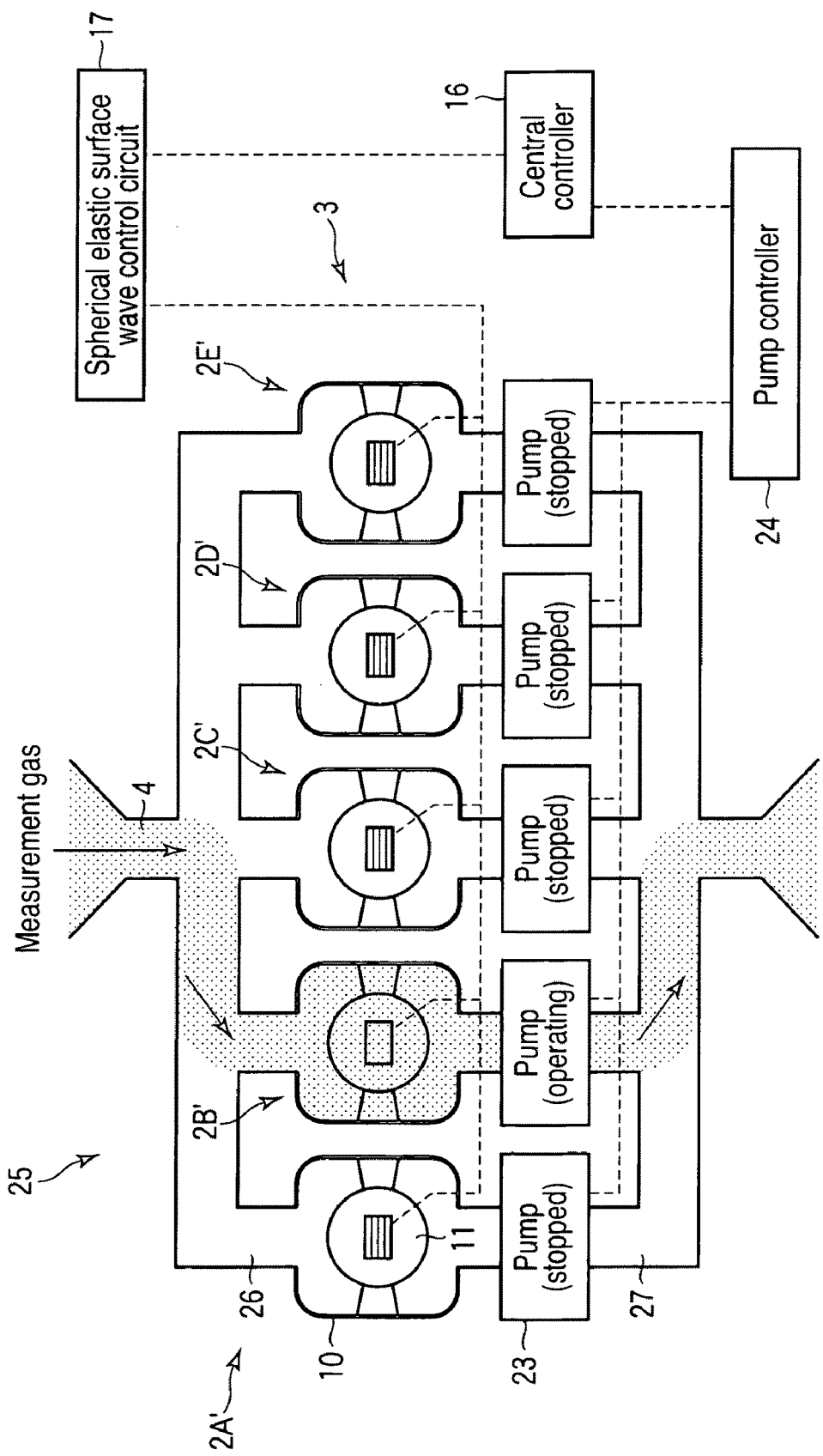
FIG. 4 is a schematic diagram showing the configuration of a fluid measurement device according to a second embodiment of the present invention.

FIG. 4 is a diagram showing the configuration of the fluid measurement device 25. A fluid measurement unit 3 of the fluid measurement device 25 according to the present embodiment includes a plurality of (five in the present embodiment) fluid measurement sections 2A' to 2E'.

The fluid measurement sections 2A' to 2E' have the same configuration. It should be noted that the configuration of one fluid measurement section 2A' is only described below as an example and the same components of the other fluid measurement sections 2B' to 2E' are provided with the same reference numbers and are not described.

The fluid measurement section 2A' includes a gas measurement chamber 10. A gas measurement sensor 11 which measures a gas as a specimen is provided in the gas measurement chamber 10. A spherical elastic surface wave element sensor is used as the gas measurement sensor 11 as in the first embodiment.

The fluid measurement section 2A' also includes an inflow duct (inflow portion) 26 and an outflow duct (outflow portion) 27. The outflow duct 27 is provided with a small pump 23. For example, a pump generally called a diaphragm is used as the small pump 23.

The small pump 23 of each of the fluid measurement sections 2A' to 2E' is connected to a pump controller (measurement controller) 24. The pump controller 24 controls the driving of the small pump 23 of each of the fluid measurement sections 2A' to 2E'. The pump controller 24 is connected to a central controller 16.

Now, the action of the fluid measurement device 25 according to the present embodiment is described. Suppose that a gas is introduced into one of the five fluid measurement sections 2A' to 2E', for example, the fluid measurement section 2B' as shown in FIG. 4. When an external gas is introduced into the fluid measurement section 2B', the small pump 23 of the fluid measurement section 2B' is driven. As a result, a suction force from the small pump 23 acts on the gas measurement chamber 10 of the fluid measurement section 2B'. Thus, a measurement fluid is introduced into the gas measurement chamber 10 of the fluid measurement section 2B from an introduction gas pipe 4. At the same time, in response to the introduction of the measurement fluid, an old gas within the gas measurement chamber 10 is discharged and exchanged for a new gas. When the gas exchange is completed, the driving of the small pump 23 of the fluid measurement section 2B' is stopped.

The second embodiment is similar to the first embodiment except for the action of introducing a gas into the fluid measurement sections 2A' to 2E'.

Therefore, if the measurement time required for one gas measurement sensor 11 is $t_0$, gas measurement operations are sequentially performed in the gas measurement chambers 10 of the fluid measurement sections 2A' to 2E' at intervals of $t_0/5$, in the fluid measurement device 25 according to the present embodiment as well. This time is 1/5 of the gas measurement time $t_0$ necessary for one gas measurement sensor 11 of each of the fluid measurement sections 2A' to 2E'. Thus, if $t_0$ is 2.2 seconds, a time resolution t' of the measurement by the fluid measurement device 25 according to the present embodiment is 0.44 seconds.

Therefore, the time resolution of the measurement by the fluid measurement device 25 is not limited by the measurement time $t_0$ necessary for one gas measurement sensor 11 of each of the fluid measurement sections 2A' to 2E'. That is, in the fluid measurement device 25, the operation of introducing a gas into the gas measurement chamber 10 of each of the fluid measurement sections 2A' to 2E' and measuring the gas is sequentially performed to provide a time difference at every set time which is shorter than the fluid measurement time $t_0$ required for one fluid measurement by the gas measurement sensor 11 of each of the fluid measurement sections 2A' to 2E'. At the same time, the respective fluid measurement sections 2A' to 2E' wait in parallel for the time in which the introduced gas acts on the sensitive film of the gas measurement sensor 11. Thus, the time resolution of the measurement by the fluid measurement device 25 is increased without being limited by the gas measurement time $t_0$ necessary for one gas measurement sensor 11 of each of the fluid measurement sections 2A' to 2E'. If the number of the fluid measurement sections 2A' to 2E' each of which includes one gas measurement sensor 11 is increased, a measurement is conducted with a higher time resolution.

Accordingly, the fluid measurement device 25 having the configuration described above has the following effects. That is, in the fluid measurement device 25 according to the present embodiment, the operation of introducing a gas into the gas measurement chamber 10 of each of the fluid measurement sections 2A' to 2E' is sequentially performed to provide a time difference at every set time which is shorter than the fluid measurement time $t_0$ required for one fluid measurement by the gas measurement sensor 11 of each of the fluid measurement sections 2A' to 2E'. As a result, the respective fluid measurement sections 2A' to 2E' wait in parallel for the time in which the introduced gas acts on the sensitive film of the gas measurement sensor 11. Thus, the time resolution of the measurement by the fluid measurement device 25 can be increased without being limited by the gas measurement time $t_0$ necessary for one gas measurement sensor 11 of each of the fluid measurement sections 2A' to 2E'. Consequently, changes in the composition and constitution of a gas can be detected with a high time resolution.

Furthermore, in the fluid measurement device 25 according to the present embodiment, the small pump 23 is used to introduce a gas into the gas measurement chamber 10 of each of the fluid measurement sections 2A' to 2E'. The discharge volume of the small pump 23 is smaller than that of the exhaust pump 15 used in the first embodiment. Thus, when the small pump 23 is used to exhaust the gas measurement chamber 10 of each of the fluid measurement sections 2A' to 2E', the pressure inside the gas measurement chamber 10 is not reduced, and the pressure inside the gas measurement chamber 10 is about the same as that of the outside air in contrast with the case where the exhaust pump 15 is used to exhaust the gas measurement chamber 10. As the phase and strength of an elastic surface wave are affected by the ambient pressure, pressure is an important factor in measuring the measurement fluid. In the fluid measurement device 25, the reduction of the pressure of the gas measurement chamber 10 of each of the fluid measurement sections 2A' to 2E' can be prevented by using the small pump 23.

In the fluid measurement device 1 according to the first embodiment, a slight opening may be made in the outflow gas valve 13 provided in the outflow duct 27 of each of the fluid measurement sections 2A to 2E even when the outflow gas valve 13 is closed. In this case, the gas is discharged from the opening of the outflow gas valve 13 by the exhaust pump 15, and thereby the state of the gas within the gas measurement chamber 10 of each of the fluid measurement sections 2A to 2E changes. The change of the gas state greatly affects the measurement of the measurement fluid. The change of the gas state can be prevented by using a precise gas valve as the outflow gas valve 13. However, the use of the precise gas valve as the outflow gas valve 13 increases costs. In contrast, in the fluid measurement device 25 according to the present embodiment, there is no movement of the gas within the gas measurement chamber 10 except during the time in which the small pump 23 of each of the fluid measurement sections 2A' to 2E' is active (the time in which a gas exchange is carried out in the gas measurement chamber 10). Thus, the change of the gas state within each gas measurement chamber 10 can be effectively prevented by using the small pump 23.

The small pump 23 is provided in the outflow duct 27 in each of the fluid measurement sections 2A' to 2E' according to the second embodiment. However, the present invention is not limited to this. For example, the inflow duct 26 of each of the fluid measurement sections 2A' to 2E' may be provided with a small pump which introduces a gas into the gas measurement chamber 10. That is, a small pump (23) which introduces a gas into the gas measurement chamber 10 when driven has only to be provided in at least one of the inflow duct 26 and the outflow duct 27.

Third Embodiment

Now, a fluid measurement device 30 according to a third embodiment is described with reference to FIG. 5. In the present embodiment, the fluid measurement device 30 obtained by modifying the configuration of the fluid measurement device 1 according to the first embodiment in the following manner is provided. It should be noted that the same parts as those in the first embodiment are provided with the same reference numbers and are not described.

Figure 5:
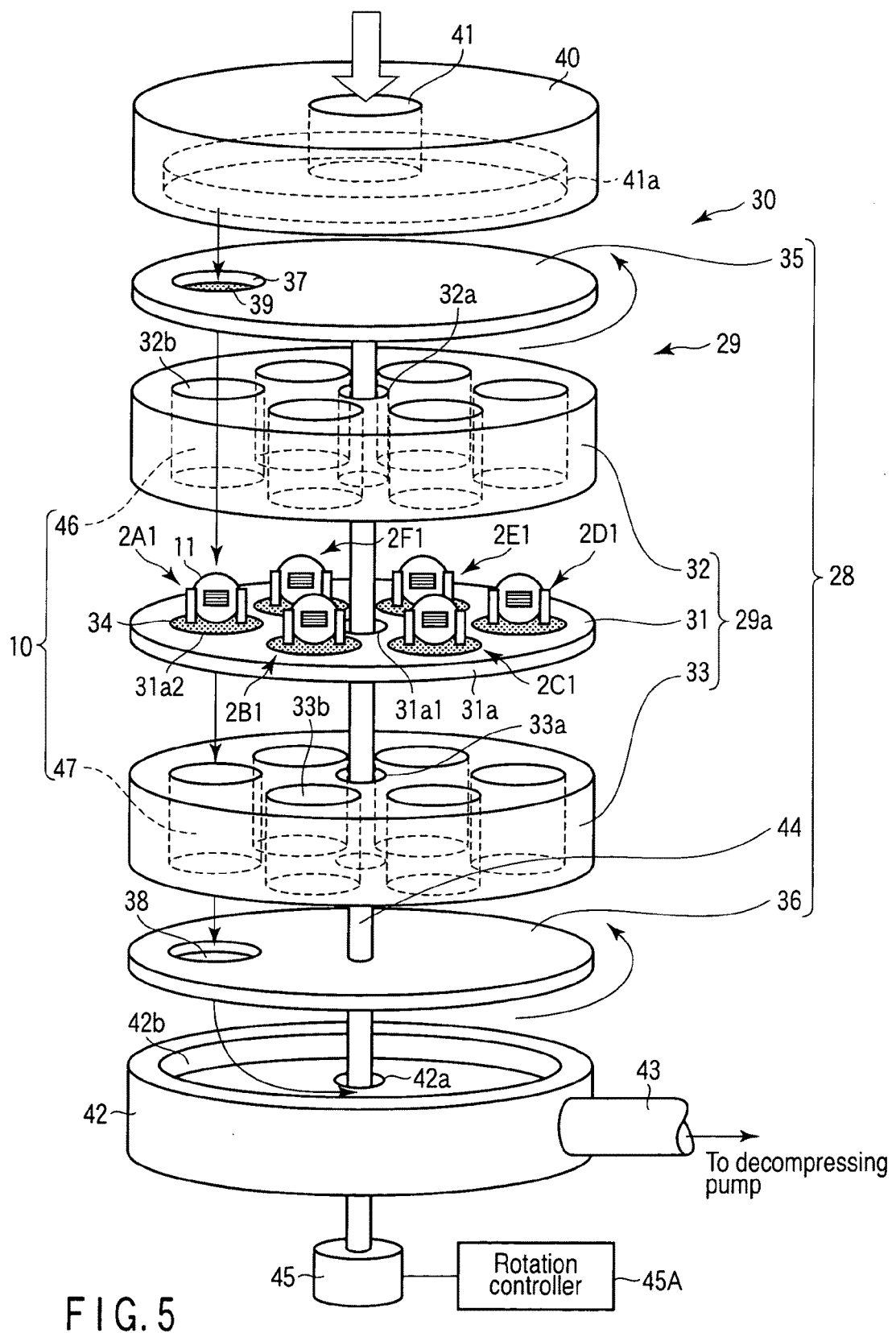
FIG. 5 is a perspective view showing the configuration of a fluid measurement device according to a third embodiment of the present invention.

FIG. 5 is a diagram showing the configuration of the fluid measurement device 30. The fluid measurement device 30 according to the present embodiment includes a fluid measurement unit 29. The fluid measurement unit 29 includes a plurality of (six in the present embodiment) fluid measurement sections 2A1 to 2F1.

The fluid measurement sections 2A1 to 2F1 are concentrically provided in the fluid measurement unit 29. Here, the fluid measurement sections 2A1 to 2F1 have the same configuration. It should be noted that the configuration of one fluid measurement section 2A1 is only described below as an example and the same components of the other fluid measurement sections 2B1 to 2F1 are provided with the same reference numbers and are not described.

The fluid measurement unit 29 includes a unit main body 29a. The unit main body 29a includes a disk-shaped sensor holder 31, an inflow container jig 32 and an outflow container jig 33. The sensor holder 31 includes a fixed disk 31a. A shaft insertion hole 31a1 is formed in the center of the fixed disk 31a. Six circular holes 31a2 are arranged at equal intervals concentrically from the shaft insertion hole 31a1 in the fixed disk 31a. A mesh filter 34 is attached to each of the circular holes 31a2. Each mesh filter 34 permits gas transmission.

A gas measurement sensor 11 which measures a gas as a specimen is provided in each mesh filter 34. A spherical elastic surface wave element sensor is used as the gas measurement sensor 11 as in the first embodiment. The gas measurement sensor 11 is connected to a spherical elastic surface wave control circuit 17 (see FIG. 1) as in the first embodiment.

In FIG. 5, the inflow container jig 32 serving as the inflow side of the gas is provided above the fixed disk 31a of the sensor holder 31, and the outflow container jig 33 serving as the outflow side of the gas is provided under the fixed disk 31a.

A shaft insertion hole 32a is formed in the center of the inflow container jig 32. Six circular holes (inflow portions) 32b are arranged at equal intervals concentrically from the shaft insertion hole 32a in the inflow container jig 32. Similarly, a shaft insertion hole 33a is formed in the center of the outflow container jig 33. Six circular holes (outflow portions) 33b are arranged at equal intervals concentrically from the shaft insertion hole 33a in the outflow container jig 33.

The unit main body 29a according to the present embodiment is formed by integrating the sensor holder 31, the inflow container jig 32 and the outflow container jig 33 so that the inflow container jig 32 is stacked on the upper side of the fixed disk 31a of the disk-shaped sensor holder 31 and the outflow container jig 33 is stacked on the lower side of the sensor holder 31. Here, each of the circular holes 31a2 of the fixed disk 31a is disposed to face a corresponding one circular hole 32b of the inflow container jig 32. Each of the circular holes 31a2 of the fixed disk 31a is also disposed to face a corresponding one circular hole 33b of the outflow container jig 33. Therefore, when the fixed disk 31a, the inflow container jig 32 and the outflow container jig 33 are stacked on one another, each of the circular holes 31a2 of the fixed disk 31a is in communication with a corresponding one circular hole 32b of the inflow container jig 32 and a corresponding one circular hole 33b of the outflow container jig 33. In this manner, six gas measurement chambers 10 which perform fluid measurement are formed within the unit main body 29a. The gas measurement sensor 11 is disposed in each of the gas measurement chambers 10, such that the gas measurement sensors 11 of the fluid measurement sections 2A1 to 2F1 are concentrically arranged in the sensor holder 31.

The fluid measurement unit 29 includes a switch section 28 which switches the inflow state of the measurement fluid into the gas measurement chamber 10 of each of the fluid measurement sections 2A1 to 2F1. The switch section 28 includes an inflow gas valve ring (inflow rotary disk) 35, an outflow gas valve ring (outflow rotary disk) 36 and a ring shaft 44.

The inflow gas valve ring 35 is disposed above the inflow container jig 32 in FIG. 5, and the outflow gas valve ring 36 is disposed under the outflow container jig 33 in FIG. 5. One inflow opening (movable inflow portion) 37 is formed in the inflow gas valve ring 35. The inflow opening 37 is located to communicate with one of the six circular holes 32b of the inflow container jig 32. One outflow opening (movable outflow portion) 38 is formed in the outflow gas valve ring 36. The outflow opening 38 is located to communicate with at least one of the six circular holes 33b of the outflow container jig 33. In the inflow opening 37, a metal mesh filter 39 is provided.

Furthermore, the ring shaft 44 is fixed to the centers of the inflow gas valve ring 35 and the outflow gas valve ring 36. The ring shaft 44 is rotatably inserted through the shaft insertion hole 32a of the inflow container jig 32 of the unit main body 29a, the shaft insertion hole 31a1 of the fixed disk 31a and the shaft insertion hole 33a of the outflow container jig 33. Further, the lower end of the ring shaft 44 is fixed to a rotary motor 45. The rotary motor 45 is connected to a rotation controller (measurement controller) 45A, and is driven and controlled by the rotation controller 45A. The ring shaft 44 is driven and rotated counterclockwise by the rotary motor 45 in FIG. 5. Together with the operation of the ring shaft 44, the inflow gas valve ring 35 and the outflow gas valve ring 36 are simultaneously driven and rotated in the same direction.

In FIG. 5, a gas introduction unit 40 is provided above the inflow gas valve ring 35. A gas introduction opening 41 is provided in the center of the gas introduction unit 40. A circular recess 41a larger in diameter than the gas introduction opening 41 is formed in the lower surface of the gas introduction unit 40. The diameter of the recess 41a is set at about the same size as the diameter of the outer peripheral edge of a ring-shaped movement track of the inflow opening 37 during the rotation of the inflow gas valve ring 35.

Furthermore, a gas exhaust unit 42 is provided under the outflow gas valve ring 36 in FIG. 5. A shaft insertion hole 42a is formed in the center of the gas exhaust unit 42. The ring shaft 44 is rotatably inserted through the shaft insertion hole 42a.

One end of a gas exhaust pipe 43 is coupled to the outer peripheral surface of the gas exhaust unit 42. The other end of the gas exhaust pipe 43 is coupled to an unshown decompressing pump. A circular recess 42b having a large diameter is formed in the upper surface of the gas exhaust unit 42. The diameter of the recess 42b is set at about the same size as the diameter of the outer peripheral edge of a ring-shaped movement track of the outflow opening 38 during the rotation of the outflow gas valve ring 36. The recess 42b is in communication with the gas exhaust pipe 43.

Now, the action of the fluid measurement device 30 according to the present embodiment is described. When the fluid measurement device 30 according to the present embodiment is in operation, the rotary motor 45 is driven and rotated, and the unshown decompressing pump is driven. In this case, the rotary motor 45 is driven and the ring shaft 44 is thereby rotated. As a result, the inflow gas valve ring 35 and the outflow gas valve ring 36 rotate around the ring shaft 44.

During the rotation of the inflow gas valve ring 35, the inflow opening 37 is brought into communication with one of the six circular holes 32b of the inflow container jig 32. For example, the inflow opening 37 is in communication with the circular hole 32b of the fluid measurement section 2A1 in FIG. 5. In this case, the circular hole 32b of the fluid measurement section 2A1 in communication with the inflow opening 37 of the inflow gas valve ring 35 serves as an inflow pipe 46 which brings a gas into the gas measurement chamber 10 of the fluid measurement section 2A1.

Furthermore, during the rotation of the outflow gas valve ring 36, the outflow opening 38 is brought into communication with one of the six circular holes 33b of the outflow container jig 33. For example, in FIG. 5, the outflow opening 38 is in communication with the circular hole 33b of the fluid measurement section 2A1. In this case, the circular hole 33b of the fluid measurement section 2A1 in communication with the outflow opening 38 of the outflow gas valve ring 36 serves as an outflow pipe 47 which brings a gas out of the gas measurement chamber 10 of the fluid measurement section 2A1.

That is, during the rotation of the inflow gas valve ring 35 and the outflow gas valve ring 36, the measurement fluid is introduced into the recess 41a from the gas introduction opening 41 of the gas introduction unit 40, for example, as indicated by an arrow in FIG. 5, by suction pressure that acts by the driving of the decompressing pump. The measurement fluid is then introduced into the gas measurement chamber 10 of one of the fluid measurement sections 2A1 to 2F1 from the inflow opening 37 of the inflow gas valve ring 35 through the mesh filter 39. At the same time, in the gas measurement chamber 10 into which the measurement fluid is introduced, the gas within the gas measurement chamber 10 is discharged to the gas exhaust pipe 43 from the outflow opening 38 of the outflow gas valve ring 36 through the recess 42b of the gas exhaust unit 42.

Suppose here that a gas is introduced into the gas measurement chamber 10 of one of the six fluid measurement sections 2A1 to 2F1, for example, the fluid measurement section 2A1 as shown in FIG. 5. In this case, as has been described in the first embodiment, there is a wait for a proper set time while the gas is being introduced, so that the introduced gas acts on the sensitive film of the gas measurement sensor 11. After the above-mentioned set time, a first burst signal is input to an interdigital electrode 22 of the gas measurement sensor 11. Further, an elastic surface wave which has revolved around an elastic surface wave revolution circuit 21 a specific number of times is measured, and its phase and strength are analyzed. The elastic surface wave is measured as many times as the predetermined number of times of averaging.

Here, the measurement time required for one gas measurement sensor 11 is $t_0$. In the fluid measurement device 30 according to the present embodiment, $t_0/6$ after the start of the introduction of the gas into the gas measurement chamber 10 of the fluid measurement section 2A1, the inflow opening 37 of the inflow gas valve ring 35 is brought into communication with the circular hole 32b of the fluid measurement section 2B1 performing the next measurement and the inflow pipe 46 is formed. Also, the outflow opening 38 of the outflow gas valve ring 36 is brought into communication with the circular hole 33b of the fluid measurement section 2B1 performing the next measurement and the outflow pipe 47 is formed. As a result, a gas measurement operation similar to that in the fluid measurement section 2A1 is performed in the gas measurement chamber 10 of the next fluid measurement section 2B1 $t_0/6$ behind the gas measurement chamber 10 of the fluid measurement section 2A1. $t_0/6$ after the start of the introduction of the gas into the gas measurement chamber 10 of the fluid measurement section 2B1, the inflow opening 37 of the inflow gas valve ring 35 is brought into communication with the circular hole 32b of the fluid measurement section 2C1 performing the next measurement, and the inflow pipe 46 is formed. Also, the outflow opening 38 of the outflow gas valve ring 36 is brought into communication with the circular hole 33b of the fluid measurement section 2C1 performing the next measurement and the outflow pipe 47 is formed. As a result, a gas measurement operation similar to that in the fluid measurement section 2B1 is performed in the gas measurement chamber 10 of the next fluid measurement section 2C1 $t_0/6$ behind the gas measurement chamber 10 of the fluid measurement section 2B1.

That is, the gas measurement operations described above are sequentially performed in the gas measurement chambers 10 of the fluid measurement sections 2A1 to 2F1 at intervals of $t_0/6$. This time is ⅙ of the gas measurement time $t_0$ necessary for one gas measurement sensor 11 of each of the fluid measurement sections 2A1 to 2F1. Thus, if $t_0$ is 2.2 seconds, a time resolution t' of the measurement by the fluid measurement device 30 according to the present embodiment is 0.37 seconds.

Therefore, the time resolution of the measurement by the fluid measurement device 30 is not limited by the measurement time $t_0$ necessary for one gas measurement sensor 11 of each of the fluid measurement sections 2A1 to 2F1. That is, in the fluid measurement device 30 according to the present embodiment, the operation of introducing a gas into the gas measurement chamber 10 of each of the fluid measurement sections 2A1 to 2F1 and measuring the gas is sequentially performed to provide a time difference at every set time which is shorter than the fluid measurement time $t_0$ required for one fluid measurement by the gas measurement sensor 11 of each of the fluid measurement sections 2A1 to 2F1. At the same time, the respective fluid measurement sections 2A1 to 2F1 wait in parallel for the time in which the introduced gas acts on the sensitive film of the gas measurement sensor 11. Thus, the time resolution of the measurement by the fluid measurement device 30 is increased without being limited by the gas measurement time $t_0$ necessary for one gas measurement sensor 11 of each of the fluid measurement sections 2A1 to 2F1. If the number of the fluid measurement sections 2A1 to 2F1 each of which includes one gas measurement sensor 11 is increased, a measurement is conducted with a higher time resolution.

Accordingly, the fluid measurement device 30 having the configuration described above has the following effects. That is, in the fluid measurement device 30 according to the present embodiment, the operation of introducing a gas into the gas measurement chamber 10 of each of the fluid measurement sections 2A1 to 2F1 can be sequentially performed to provide a time difference at every set time which is shorter than the fluid measurement time $t_0$ required for one fluid measurement by the gas measurement sensor 11 of each of the fluid measurement sections 2A1 to 2F1. As a result, the respective fluid measurement sections 2A1 to 2F1 wait in parallel for the time in which the introduced gas acts on the sensitive film of the gas measurement sensor 11. Thus, the time resolution of the measurement by the fluid measurement device 30 can be increased without being limited by the gas measurement time $t_0$ necessary for one gas measurement sensor 11 of each of the fluid measurement sections 2A1 to 2F1. Consequently, changes in the composition and constitution of a gas can be detected with a high time resolution.

In addition, the fluid measurement sections 2A1 to 2F1 do not necessarily have to be concentrically arranged if the gas is sequentially exchanged in the gas measurement chamber 10 of one of the fluid measurement sections 2A1 to 2F1.

Fourth Embodiment

Now, a fluid measurement device 48 according to a fourth embodiment of the present invention is described with reference to FIG. 6A. In the present embodiment, the fluid measurement device 48 obtained by modifying the configuration of the fluid measurement device 30 according to the third embodiment in the following manner is provided. It should be noted that the same parts as those in the third embodiment are provided with the same reference numbers and are not described.

Figure 6A:
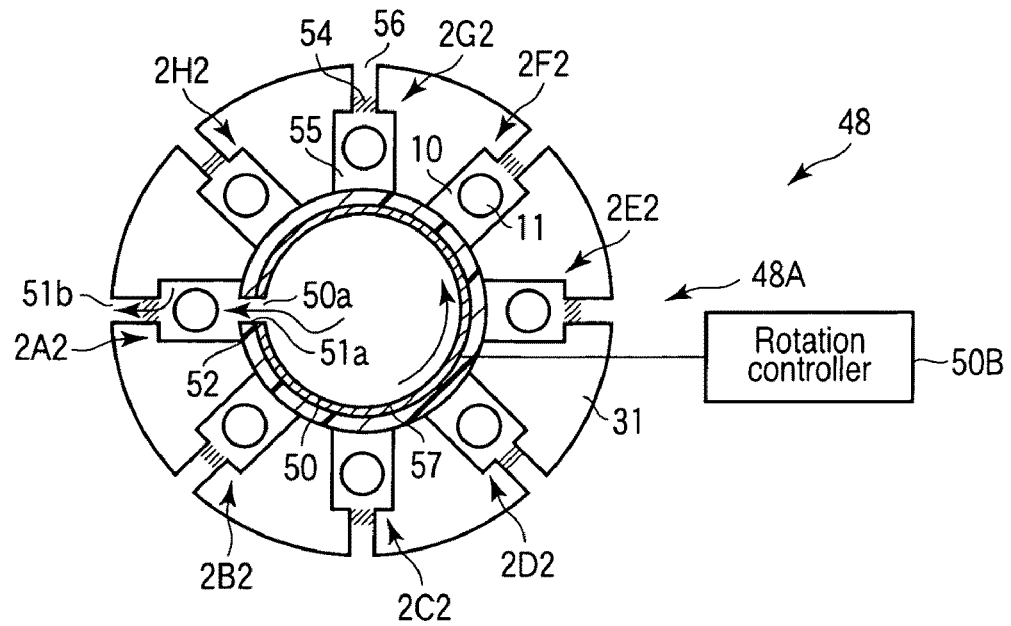
FIG. 6A is a schematic diagram showing the configuration of a fluid measurement device according to a fourth embodiment of the present invention.

FIG. 6A is a diagram showing the overall rough configuration of the fluid measurement device 48. The fluid measurement device 48 according to the present embodiment includes a fluid measurement unit 48A. The fluid measurement unit 48A includes a plurality of (eight in the present embodiment) fluid measurement sections 2A2 to 2H2.

The fluid measurement device 48 according to the present embodiment includes a substantially cylindrical sensor holder 31, and a gas supply cylinder (fluid supply cylinder) 50 disposed inside the sensor holder 31. Gas measurement chambers 10 of the fluid measurement sections 2A2 to 2H2 are concentrically arranged side by side in the sensor holder 31. Here, the fluid measurement sections 2A2 to 2H2 have the same configuration. It should be noted that the configuration of one fluid measurement section 2A2 is only described below as an example and the same components of the other fluid measurement sections 2B2 to 2H2 are provided with the same reference numbers and are not described.

An inflow opening (inflow portion) 51a leading to the gas measurement chamber 10 of each of the fluid measurement sections 2A2 to 2H2 is formed in the inner peripheral surface of the sensor holder 31. Moreover, an outflow opening (outflow portion) 51b leading out of the gas measurement chamber 10 of each of the fluid measurement sections 2A2 to 2H2 is formed in the outer peripheral surface of the sensor holder 31. In each of the fluid measurement sections 2A2 to 2H2, an inflow duct 55 is formed to extend from the inflow opening 51a provided in the inner peripheral surface of the sensor holder 31. Also, in each of the fluid measurement sections 2A2 to 2H2, an outflow duct 56 is formed to extend to the outflow opening 51b provided in the outer peripheral surface of the sensor holder 31. Thus, the inflow duct 55 extends in the diametrical direction of the sensor holder 31 on the inner peripheral side of the gas measurement chamber 10, and the outflow duct 56 extends in the diametrical direction of the sensor holder 31 on the outer peripheral side of the gas measurement chamber 10.

A resistance filter 54 is provided in each outflow duct 56. Even for a short time, the resistance filter 54 of each of the fluid measurement sections 2A2 to 2H2 inhibits, for example, the natural external leakage of the gas within the gas measurement chamber 10 and the entry of an external gas into the gas measurement chamber 10.

A gas measurement sensor 11 which measures a gas as a specimen is provided in the gas measurement chamber 10 of the fluid measurement section 2A2. A spherical elastic surface wave element sensor is used as the gas measurement sensor 11 as in the first embodiment. The gas measurement sensor 11 is connected to a spherical elastic surface wave control circuit 17 (see FIG. 1) as in the first embodiment.

The gas supply cylinder 50 is connected to a rotation controller (measurement controller) 50B. The gas supply cylinder 50 is driven and rotated counterclockwise by the rotation controller 50B in FIG. 6A around the axial center position of the sensor holder 31. The outer peripheral surface of the gas supply cylinder 50 is provided with one gas supply opening (movable inflow portion) 50a which can be in communication with the inflow opening 51a of the gas measurement chamber 10 of one of the eight fluid measurement sections 2A2 to 2H2.

The gas as a specimen is then supplied from a direction perpendicular to the surface of the drawing within the gas supply cylinder 50 in FIG. 6A. Together with the rotation of the gas supply cylinder 50, the inflow opening 51a of one of the eight fluid measurement sections 2A2 to 2H2 is brought into communication with the gas supply opening 50a of the gas supply cylinder 50 in turn. As a result, the gas supply opening 50a is in communication with the inflow opening 51a of one of the fluid measurement sections 2A2 to 2H2 during the rotation of the gas supply cylinder 50. The gas measurement chambers 10 are brought into communication with the gas supply opening 50a in turn. A gas is then introduced into the gas measurement chamber 10 through the gas supply opening 50a. In this manner, a switch section 57 is configured. The switch section 57 includes the gas supply cylinder 50, and switches the flow of a measurement fluid into the gas measurement chamber 10 of each of the fluid measurement sections 2A2 to 2H2.

A gas sealing elastic resin 52 is attached to the outer peripheral surface of the gas supply cylinder 50. When the gas is measured by the gas measurement sensor 11, the gas within the gas measurement chamber 10 of each of the fluid measurement sections 2A2 to 2H2 is held by the elastic resin 52.

Now, the action of the fluid measurement device 48 according to the present embodiment is described. When the fluid measurement device 48 according to the present embodiment is in operation, the gas supply cylinder 50 is driven and rotated counterclockwise in FIG. 6A. The gas as a specimen is supplied from the direction perpendicular to the surface of the drawing within the gas supply cylinder 50 in FIG. 6A. Suppose here that a gas is introduced into the gas measurement chamber 10 of one of the eight fluid measurement sections 2A2 to 2H2, for example, the fluid measurement section 2A2 as shown in FIG. 6A. In this case, the gas supply opening 50a of the gas supply cylinder 50 is in communication with the inflow duct 55 of the fluid measurement section 2A2.

The gas is then introduced into the gas measurement chamber 10 through the fluid measurement section 2A2. In this case, as has been described in the first embodiment, there is a wait for a proper set time so that the introduced gas acts on the sensitive film of the gas measurement sensor 11. After the above-mentioned set time, a first burst signal is input to an interdigital electrode 22 of the gas measurement sensor 11. Further, an elastic surface wave which has revolved around an elastic surface wave revolution circuit 21 a specific number of times is measured, and its phase and strength are analyzed. The elastic surface wave is measured as many times as the predetermined number of times of averaging.

Here, the measurement time required for one gas measurement sensor 11 is $t_0$. $t_0/8$ after the start of the introduction of the gas into the gas measurement chamber 10 of the fluid measurement section 2A2, the gas supply opening 50a of the gas supply cylinder 50 is brought into communication with the inflow duct 55 of the fluid measurement section 2B2 performing the next measurement. As a result, a gas measurement operation similar to that in the fluid measurement section 2A2 is performed in the gas measurement chamber 10 of the next fluid measurement section 2B2 $t_0/8$ behind the gas measurement chamber 10 of the fluid measurement section 2A2. Further, $t_0/8$ after the start of the introduction of the gas into the gas measurement chamber 10 of the fluid measurement section 2B2, the gas supply opening 50a of the gas supply cylinder 50 is brought into communication with the inflow duct 55 of the fluid measurement section 2C2 performing the next measurement. As a result, a gas measurement operation similar to that in the fluid measurement section 2B2 is performed in the gas measurement chamber 10 of the next fluid measurement section 2C2 $t_0/8$ behind the gas measurement chamber 10 of the fluid measurement section 2B2.

That is, the gas measurement operations described above are sequentially performed in the gas measurement chambers 10 of the fluid measurement sections 2A2 to 2H2 at intervals of $t_0/8$. This time is 1/8 of the gas measurement time $t_0$ necessary for one gas measurement sensor 11 of each of the fluid measurement sections 2A2 to 2H2. Thus, if $t_0$ is 2.2 seconds, a time resolution t' of the measurement by the fluid measurement device 48 according to the present embodiment is 0.28 seconds.

Therefore, the time resolution of the measurement by the fluid measurement device 48 is not limited by the measurement time $t_0$ necessary for one gas measurement sensor 11 of each of the fluid measurement sections 2A2 to 2H2. That is, in the fluid measurement device 48 according to the present embodiment, the operation of introducing a gas into the gas measurement chamber 10 of each of the fluid measurement sections 2A2 to 2H2 and measuring the gas is sequentially performed to provide a time difference at every set time which is shorter than the fluid measurement time $t_0$ required for one fluid measurement by the gas measurement sensor 11 of each of the fluid measurement sections 2A2 to 2H2. At the same time, the respective fluid measurement sections 2A2 to 2H2 wait in parallel for the time in which the introduced gas acts on the sensitive film of the gas measurement sensor 11. Thus, the time resolution of the measurement by the fluid measurement device 48 can be increased without being limited by the gas measurement time $t_0$ necessary for one gas measurement sensor 11 of each of the fluid measurement sections 2A2 to 2H2. If the number of the fluid measurement sections 2A2 to 2H2 each of which includes one gas measurement sensor 11 is increased, a measurement is conducted with a higher time resolution.

Accordingly, the fluid measurement device 48 having the configuration described above has the following effects. That is, in the fluid measurement device 48 according to the present embodiment, the operation of introducing a gas into the gas measurement chamber 10 of each of the fluid measurement sections 2A2 to 2H2 can be sequentially performed to provide a time difference at every set time which is shorter than the fluid measurement time $t_0$ required for one fluid measurement by the gas measurement sensor 11 of each of the fluid measurement sections 2A2 to 2H2. As a result, the respective fluid measurement sections 2A2 to 2H2 wait in parallel for the time in which the introduced gas acts on the sensitive film of the gas measurement sensor 11. Thus, the time resolution of the measurement by the fluid measurement device 48 can be increased without being limited by the gas measurement time $t_0$ necessary for one gas measurement sensor 11 of each of the fluid measurement sections 2A2 to 2H2. Consequently, changes in the composition and constitution of a gas can be detected with a high time resolution.

Figure 6B:
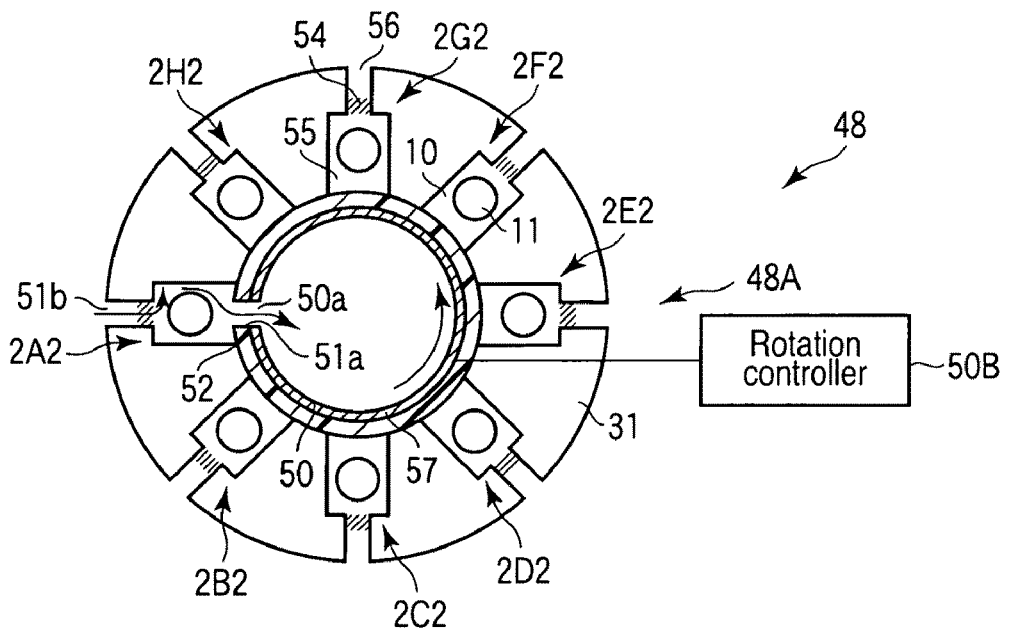
FIG. 6B is a schematic diagram showing the configuration of a fluid measurement device according to a modification of the fourth embodiment.

In the present embodiment, the measurement fluid is sent by positive pressure to the gas measurement chambers 10 of 2A2 to 2H2 arranged concentrically from the rotary gas supply cylinder 50. However, the present invention is not limited to this. As shown in FIG. 6B as a modification, the inflow opening and the outflow opening may be interchanged so that the measurement gas is introduced from the outer peripheral side by negative pressure from the gas supply cylinder (fluid supply cylinder) 50 and measured in each of the fluid measurement sections 2A2 to 2H2. In this case, during the rotation of the gas supply cylinder 50, the gas outflow opening (movable outflow portion) 50a is in communication with the outflow opening (outflow portion) 51a of one of the fluid measurement sections 2A2 to 2H2.

Moreover, although the gas (gaseous body) is the measurement target in the fluid measurement devices according to the first to fourth embodiments of the present invention, a similar operation is performed even when the measurement target is a liquid.

Fifth Embodiment

Figure 7:
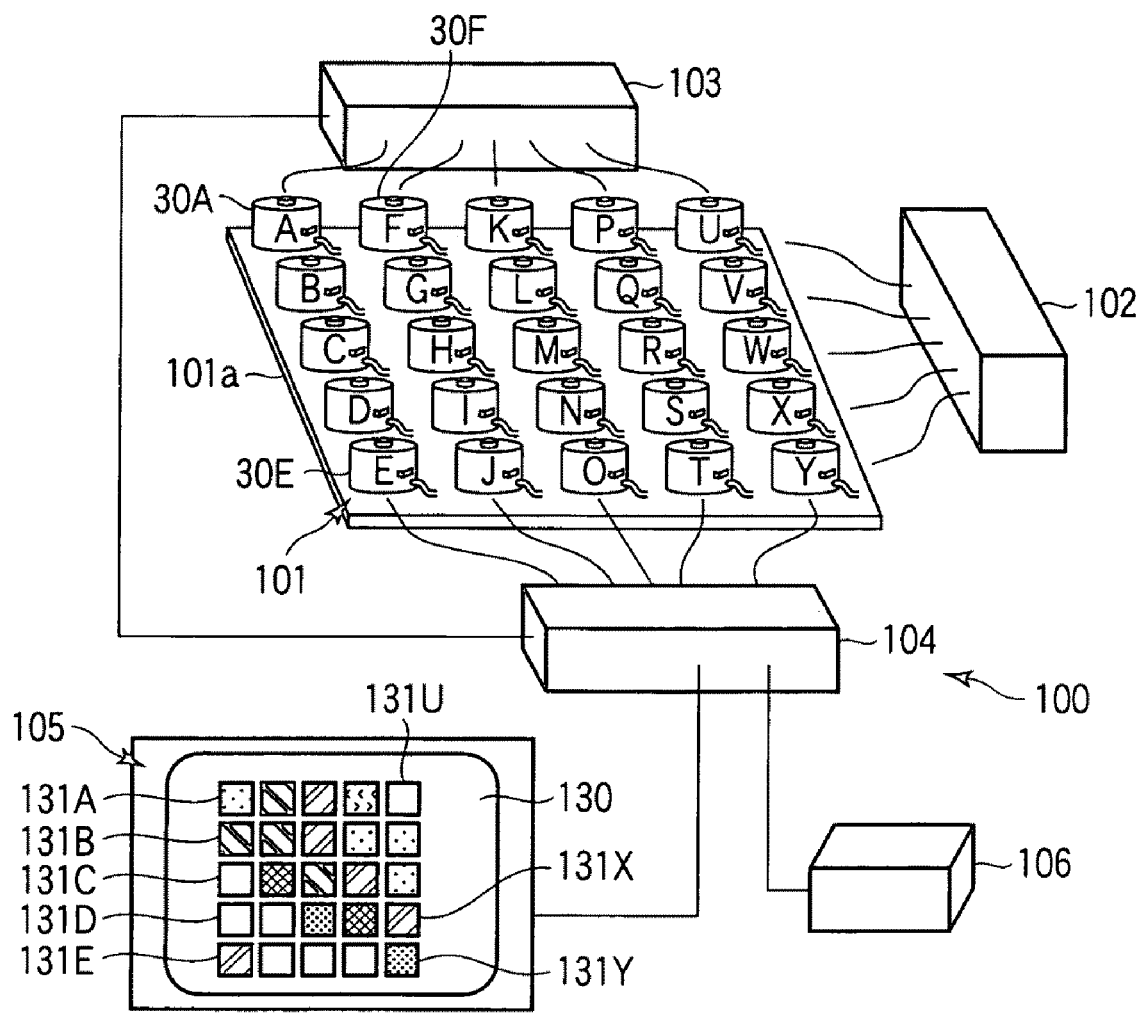
FIG. 7 is a schematic diagram showing the configuration of a fluid spacial distribution visualization device according to a fifth embodiment of the present invention.

Now, a fifth embodiment of the present invention is described with reference to FIG. 7 to FIG. 11. FIG. 7 is a diagram showing a rough configuration of a fluid spacial distribution visualization device 100 that uses, for example, the fluid measurement device 30 according to the third embodiment (see FIG. 5).

The fluid spacial distribution visualization device 100 includes a distribution measurement unit 101 and a display unit 105. The distribution measurement unit 101 includes a substantially rectangular support plate 101a and a plurality of (25 in the present embodiment) fluid measurement devices 30. Each of the fluid measurement devices 30 has the same configuration as that of the fluid measurement device 30 according to the third embodiment (see FIG. 5). Twenty-five fluid measurement devices 30 are two-dimensionally arranged on the support plate 101a so that five fluid measurement devices 30 are arranged in each of longitudinal and lateral directions. For convenience of explanation, the 25 fluid measurement devices 30 are indicated by the reference numbers A to Y in order in the longitudinal and lateral directions as shown in FIG. 7.

The fluid spacial distribution visualization device 100 further includes an exhaust unit 102, a motor control unit (measurement control unit) 103 and a central control unit 104. The exhaust unit 102 is connected to a gas exhaust pipe 43 of each of the fluid measurement devices 30A to 30Y of the distribution measurement unit 101. For example, a pump is incorporated in the exhaust unit 102 to decompress and exhaust the fluid measurement devices 30A to 30Y.

The motor control unit 103 is connected to the rotary motor 45 of each of the fluid measurement devices 30A to 30Y. The motor control unit (rotation control unit) 103 controls the rotation of the inflow gas valve ring 35, the outflow gas valve ring 36 and the ring shaft 44 of each of the fluid measurement devices 30A to 30Y. Thus, in each of the fluid measurement devices 30A to 30Y, a gas exchange is sequentially performed in the gas measurement chamber 10 of one of the fluid measurement sections 2A1 to 2F1 every $t_0/6$.

The central control unit 104 is connected to the fluid measurement devices 30A to 30Y. The central control unit 104 inputs a burst signal to each of the fluid measurement devices 30A to 30Y, and receives an output result.

The display unit 105 and an input unit 106 are connected to the central control unit 104. The display unit 105 is a general display or a touch-panel display. The display unit 105 includes a display screen 130. As many (25 in the present embodiment) display elements 131 as the fluid measurement devices 30 are provided in the display screen 130.

Figure 8:
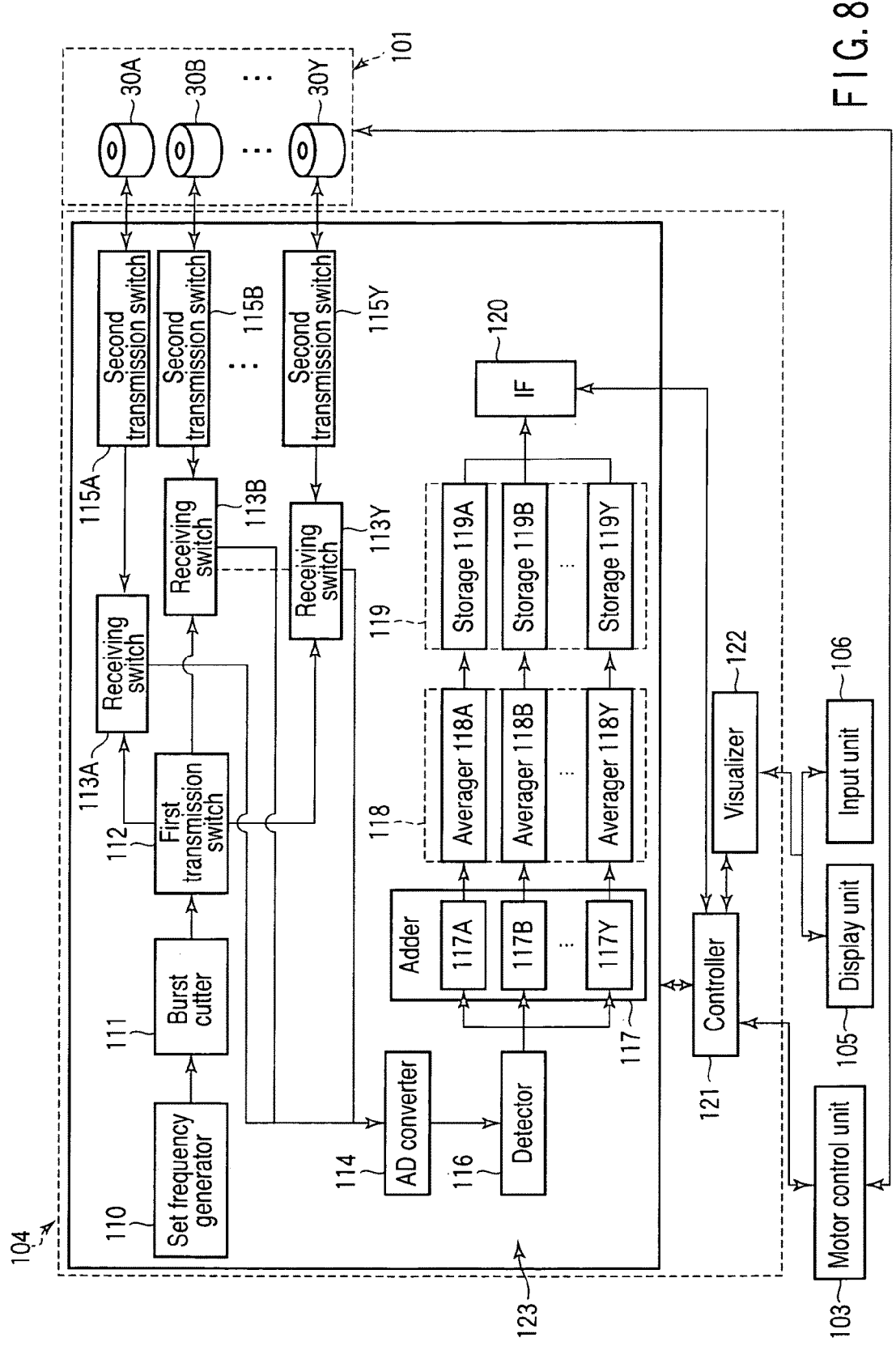
FIG. 8 is a block diagram showing the configuration of the fluid spacial distribution visualization device according to the fifth embodiment.

FIG. 8 is a block diagram showing the configuration of the fluid spacial distribution visualization device 100. As shown in FIG. 8, the central control unit 104 includes a computation unit 123, a controller 121 and a visualizer 122. The visualizer 122 visualizes, in the display screen 130, changes of a fluid obtained from measurement data in the fluid measurement devices 30A to 30Y. In order to display measurement results in the fluid measurement devices 30A to 30Y in the display screen 130, the visualizer 122 detects the display elements 131A to 131Y arranged at positions corresponding to the fluid measurement devices 30A to 30Y in the display screen 130. For example, the display element 131A is disposed at a position corresponding to the fluid measurement device 30A in the display screen 130. Thus, measurement results of the measurement fluid in the fluid measurement devices 30A to 30Y are displayed on the display elements 131A to 131Y arranged at the corresponding positions in the display screen 130. As a result, gas distribution changes and task status are displayed on the display unit 105.

The computation unit 123 includes a set frequency generator 110 which generates a high-frequency signal. The set frequency generator 110 is connected to a burst cutter 111. The burst cutter 111 is a switch component which cuts, by any set time length, the high-frequency signal generated in the set frequency generator 110. In this manner, a high-frequency burst signal is generated.

The burst cutter 111 is connected to a first transmission switch 112. The first transmission switch 112 inputs the high-frequency burst signal cut by the burst cutter 111 to the fluid measurement devices 30A to 30Y in turn. Each of the fluid measurement devices 30A to 30Y includes the fluid measurement sections 2A1 to 2F1. The gas measurement sensor 11 is provided in each of the fluid measurement sections 2A1 to 2F1. The first transmission switch 112 sequentially switches the fluid measurement devices 30A to 30Y to input the high-frequency burst signal every time equal to or more than a revolution time in which the elastic surface wave makes a round of the elastic surface wave revolution circuit 21 of the gas measurement sensor 11. For a high-frequency burst signal of 150 MHz, the input destination is switched every time equal to or more than 1 μs when the diameter of the spherical elastic surface wave element 20 of the gas measurement sensor 11 is 1 mm, or every about 3.3 μs when the diameter of the spherical elastic surface wave element 20 is 3.3 mm.

When the time at which the input destination of the high-frequency burst signal is switched to each of the fluid measurement devices 30A to 30Y coincides with the time at which an output signal from one of the fluid measurement devices 30A to 30Y is detected, the first transmission switch 112 waits without inputting the high-frequency burst signal to the fluid measurement devices 30A to 30Y as the input destination. Thus, there is no influence of an input signal during the detection of the output signal, so that the output signal can be detected with great accuracy.

The first transmission switch 112 is connected to receiving switches 113A to 113Y. As many receiving switches 113A to 113Y as the fluid measurement devices 30A to 30Y are provided. Each of the receiving switches 113A to 113Y extracts a revolution signal of the elastic surface wave from a corresponding one of the fluid measurement devices 30A to 30Y. The extracted revolution signal is sent to an AD converter 114 as an output signal from each of the fluid measurement devices 30A to 30Y.

The receiving switches 113A to 113Y are connected to corresponding second transmission switches 115A to 115Y, respectively. All of the second transmission switches 115A to 115Y have the same configuration. It should be noted that the configuration of one second transmission switch 115A is only described below as an example and the same components of the other second transmission switches 115B to 115Y are provided with the same reference numbers and are not described. The second transmission switch 115A is connected to the corresponding fluid measurement device 30A. The second transmission switch 115A inputs a high-frequency burst signal to the gas measurement sensor 11 provided, in each of the fluid measurement sections 2A1 to 2F1 of the fluid measurement device 30A. The input destination of the high-frequency burst signal is sequentially switched in accordance with how the gas flows into the gas measurement chamber 10 of each of the fluid measurement sections 2A1 to 2F1 of the fluid measurement device 30A. In the present embodiment, the second transmission switch 115A sequentially switches, every $t_0/6$, the fluid measurement sections 2A1 to 2F1 to input the high-frequency burst signal.

The AD converter (ADC) 114 is a unit which converts an analog output signal into a digital signal. In addition, an output signal from each of the fluid measurement devices 30A to 30Y is input to the AD converter 114 at an interval equal to the time of switching by the first transmission switch 112. As a result, the output signals from the respective fluid measurement devices 30A to 30Y are separated from one another and are sequentially output at times different from one another. Therefore, one AD converter 114 is enough. The AD converter 114 is connected to a detector 116. The detector 116 converts the output signal digitized by the AD converter 114 into phase/strength data.

The detector 116 is connected to an adder 117. The adder 117 adds together the phase/strength data calculated by the detector 116. The adder 117 includes addition regions 117A to 117Y corresponding to the fluid measurement devices 30A to 30Y. The added data is temporarily saved in each of the addition regions 117A to 117Y.

The adder 117 is connected to averagers 118A to 118Y. Each of the averagers 118A to 118Y computes data. When the high-frequency burst signals of the first fluid measurement device 30A to the last fluid measurement device 30Y are repeatedly input as many times as the number of times of averaging set by the controller 121, the averagers 118A to 118Y average the output signals from the corresponding fluid measurement devices 30A to 30Y, respectively. As the influence of noise is greater in one measurement alone, the data is measured more than one time. That is, after measurement data of the fluid measurement device 30Y is stored, measurements are again started with the first fluid measurement device 30A. In addition, the second and following measurements have to be conducted after the influence of the revolution of the previous elastic surface wave has disappeared. Therefore, for example, when conducting the second and following measurements, the fluid measurement device 30A waits for 1 ms or more after the input of the previous elastic surface wave.

The averagers 118A to 118Y are connected to corresponding storages 119A to 119Y, respectively. The storages 119A to 119Y store the data averaged by the corresponding averagers 118A to 118Y as data of corresponding fluid measurement devices 30A to 30Y, respectively. Although as many storages 119A to 119Y as the fluid measurement devices 30A to 30Y are provided in the present embodiment, the data in the fluid measurement devices 30A to 30Y may be saved, for example, in a single storage 19 separately by addresses for the respective fluid measurement devices 30A to 30Y. Moreover, data may be sequentially saved in a storage 119 for the respective fluid measurement devices 30A to 30Y, and the data may be sent to, for example, an external personal computer (PC) from the storage 119.

An interface (IF) 120 enables data to be relayed between the computation unit 123 and the controller 121. Specifically, the interface 120 is, for example, a USB, Ethernet (registered trademark), Bluetooth (registered trademark), IEEE-1394, PHS, WCDMA, CDMA2000 or IEEE-802.xx, and is capable of transferring a command or data whether in a wired or wireless manner.

The controller 121 is a computer which controls the whole system of the fluid spacial distribution visualization device 100. As described above, the controller 121 visualizes, in the display screen 130, a change of a fluid obtained from measurement data in each of the fluid measurement devices 30A to 30Y. The controller 121 also controls the frequency of the high-frequency burst signal, adjusts the length of the burst signal, controls the switching by the first transmission switch 112 and controls the switching of the receiving switches 113A to 113Y. Thus, a measurement program is executed, and the response measurement of the elastic wave is started.

Furthermore, the controller 121 controls the switching of the second transmission switches 115A to 115Y on the basis of information from the motor control unit 103. The controller 121 also sets the number of times of averaging and controls the computations by the averagers 118A to 118Y. The controller 121 then measures response characteristics of the elastic surface waves from the corresponding fluid measurement devices 30A to 30Y on the basis of the output signals averaged by the averagers 118A to 118Y, respectively. Moreover, the controller 121 communicates with other computers, controls the display unit 105, receives data input from the input unit 106, and processes errors of input numerical values.

The input unit 106 is, for example, a general keyboard or mouse, an exclusive input unit, or a touch-panel display. The input unit 106 enables the input of, for example, various set values of the computation unit 123 (central control unit 104), the frequency of the burst signal, the length of the burst signal, and the number of times of averaging.

Figure 9A:
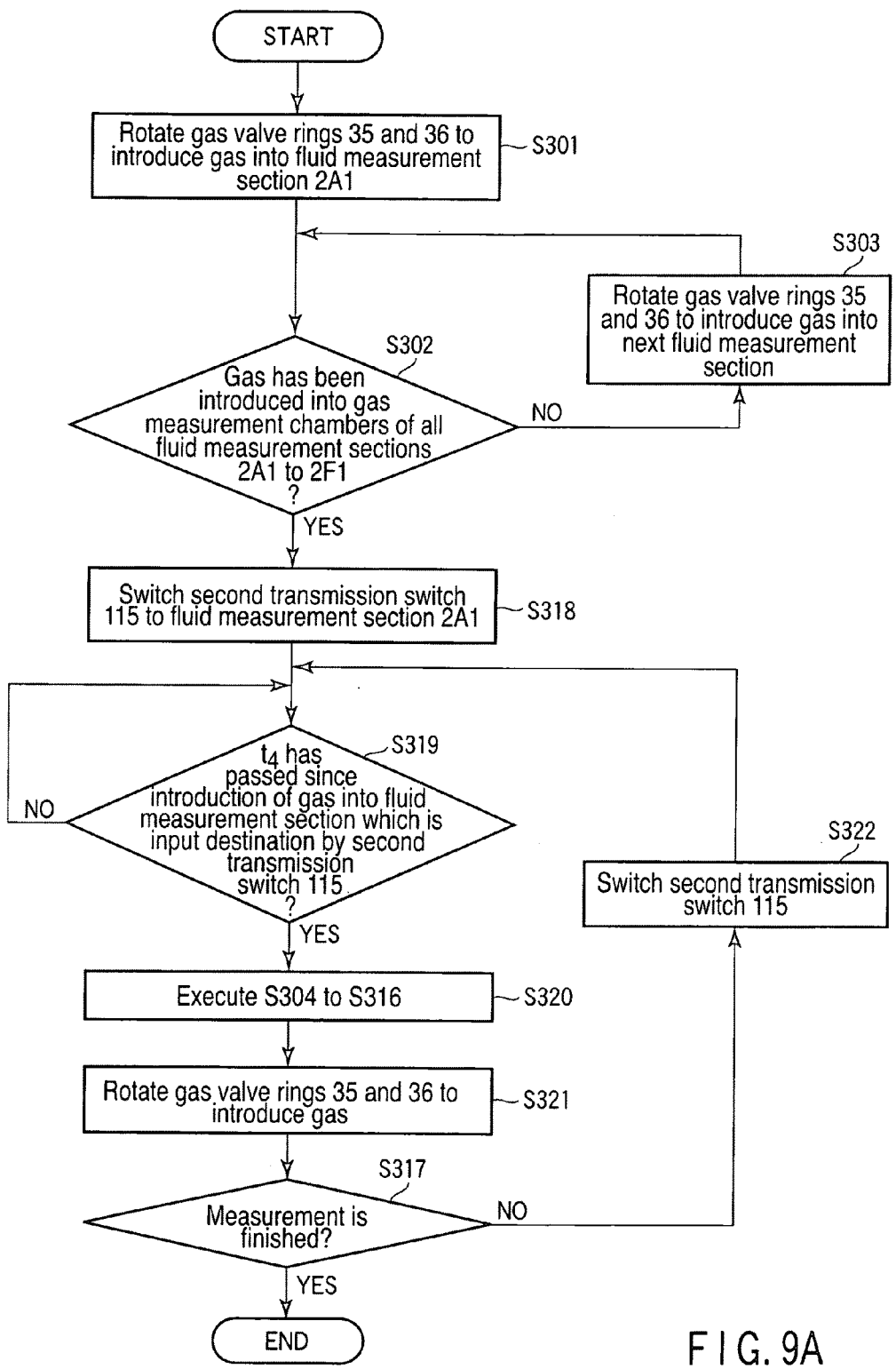
FIG. 9A is a flowchart showing the operation of the fluid spacial distribution visualization device according to the fifth embodiment.
Figure 9B:
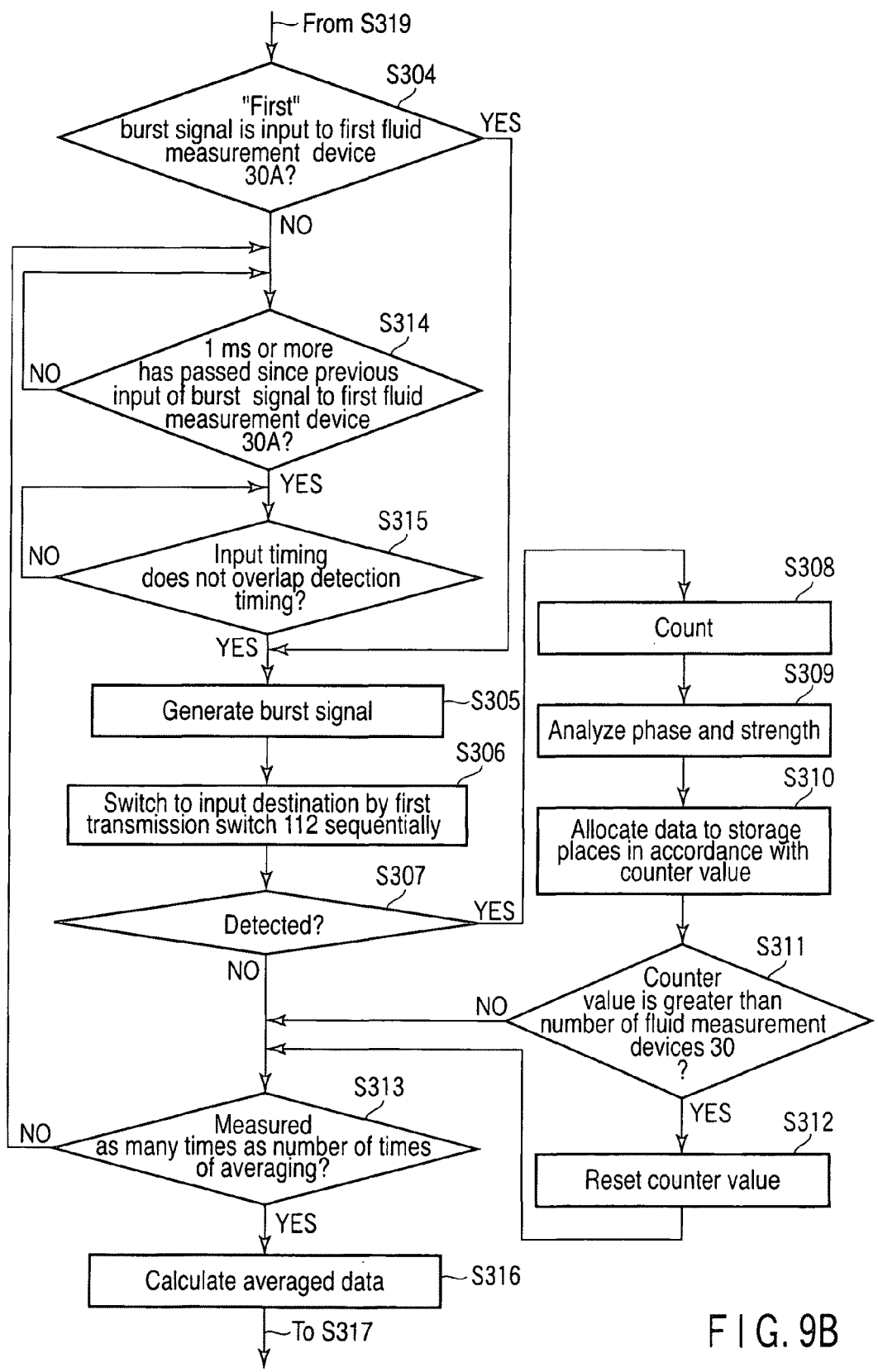
FIG. 9B is a flowchart showing the operation in step S320 of FIG. 9A.
Figure 10:
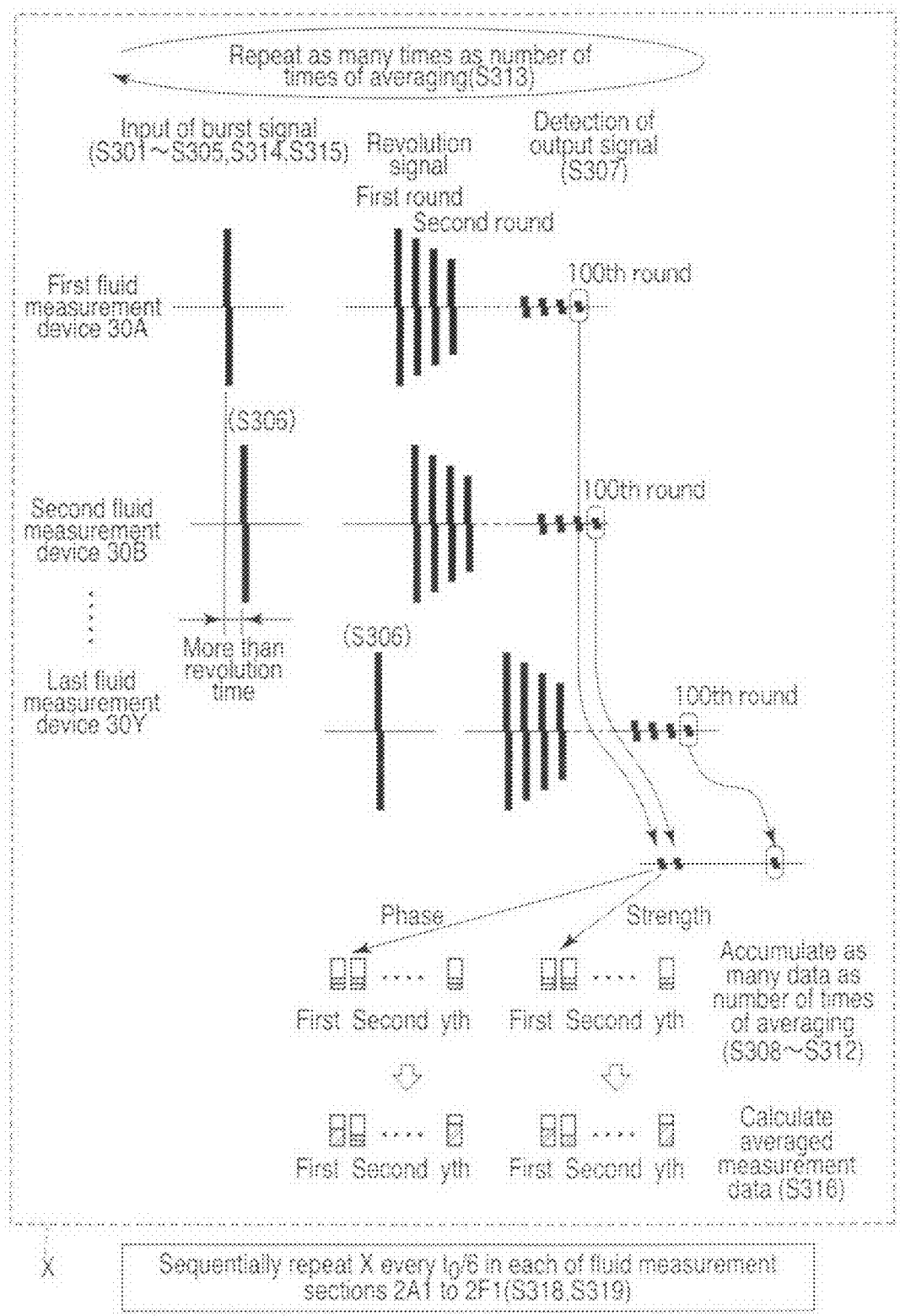
FIG. 10 is a schematic diagram illustrating the action of the fluid spacial distribution visualization device according to the fifth embodiment.

Now, the action of the fluid spacial distribution visualization device 100 according to the present embodiment is described with reference to FIG. 9A to FIG. 10. Operations in steps S301 to S303, S318, S319, S321 and S322 below apply to all of the fluid measurement devices 30A to 30Y. Therefore, the operation in one fluid measurement device 30A is only described here as an example, and the operations in the other fluid measurement devices 30B to 30Y are not described.

First, in the fluid measurement device 30A, a gas is introduced into the gas measurement chamber 10 of one of the fluid measurement sections 2A1 to 2F1, for example, the fluid measurement section 2A1. Further, the inflow gas valve ring 35 and the outflow gas valve ring 36 are rotated, and the measurement gas is sequentially introduced into the gas measurement chambers 10 of the other fluid measurement sections 2B1 to 2F1 (steps S301 and S303). When the introduction of the gas into the gas measurement chambers 10 of all of the fluid measurement sections 2A1 to 2F1 is completed, the second transmission switch 115 is switched to the fluid measurement section 2A1, and a measurement is started with the fluid measurement section 2A1 (steps S302—YES, S318). Here, as described above, the operations in steps S301 to S303 can be performed in parallel for all of the fluid measurement devices 30A to 30Y. Further, there is a wait until the gas completes its action on the sensitive film of the gas measurement sensor 11 of the fluid measurement section 2A1 of the fluid measurement device 30A (step S319). When the action of the gas on the sensitive film is completed, measurement steps shown in FIG. 9B are performed (steps S304 to S316). A time $t_4$ required from the introduction of the gas to the completion of the action of the gas on the sensitive film of the gas measurement sensor 11 is 2.1 seconds because the gas exchange time $t_1$ is 0.1 seconds and the time $t_2$ of the gas action on the sensitive film is 2.0 seconds as described above (when the spherical elastic surface wave element 20 having a diameter of 3.3 mm is used).

Here, in the operations in steps S304 to S316 shown in FIG. 9B, the computation unit 123 and the controller 121 are used to conduct a measurement rapidly and in parallel at the point where the introduction of the gas and the action on the sensitive film are finished in the fluid measurement devices 30A to 30Y as described above. When the signal is input to the first fluid measurement device 30A first time, a high-frequency burst signal used as input is generated via the burst cutter 111 (steps S304—YES, S305). The burst cutter 111 generates a high-frequency burst signal having a set length shorter than a revolution time in which the elastic surface wave makes a round of the elastic surface wave revolution circuit 21 of the gas measurement sensor 11. As a result, the signals output from the fluid measurement devices 30A to 30Y are separated in terms of time.

Next, the high-frequency burst signal is input to the gas measurement sensor 11 of the fluid measurement section 2A of the first fluid measurement device 30A via the first transmission switch 112, the receiving switch 113A and the second transmission switch 115A. When the high-frequency burst signal is input to the first fluid measurement device 30A, the first transmission switch 112 sequentially switches the input destination of the high-frequency signal to the other fluid measurement devices 30B to 30Y (step S306). In this case, before a detection time at which the output signal from the first fluid measurement device 30A is detected, the first transmission switch 112 sequentially switches the input destination of the high-frequency burst signal to the other fluid measurement devices 30B to 30Y. Moreover, the second transmission switch 115A is switched to a condition in which the high-frequency burst signal is input to the gas measurement sensor 11 of the fluid measurement section 2A of the fluid measurement device 30A. The second transmission switches 115B to 115Y are also switched to a condition in which the high-frequency burst signal is input to the gas measurement sensors 11 of the fluid measurement sections 2A of the corresponding fluid measurement devices 30B to 30Y. When the high-frequency burst signal is input, the elastic surface wave makes a round of the elastic surface wave revolution circuit 21 of the gas measurement sensor 11.

Furthermore, after the output from the first fluid measurement device 30A is detected, the output signals of the first fluid measurement device 30A to the last fluid measurement device 30Y are sequentially detected via the corresponding receiving switches 113A to 113Y (step S307—YES). In the present embodiment, since the revolution signal in the case where the elastic surface wave makes 100 rounds is targeted in measurement, output signals are sequentially detected 330 µs after the high-frequency burst signal is input to the first fluid measurement device 30A (when the spherical elastic surface wave element 20 having a diameter of 3.3 mm is used).

In the detection, a counter value indicating the number of detected signals is counted (step S308). Further, phase data and strength data are obtained by the detector 116 from the output signal digitized by the analog-to-digital (AD) converter 114 (step S309). The data is then allocated to data storage places of the adder 117 on the basis of the counter value (step S310). When the counter value is greater than the total number of the fluid measurement devices 30A to 30Y, this value is reset (steps S311—YES, S312). Thus, the counter value can be associated with each of the fluid measurement devices 30A to 30Y.

Furthermore, response characteristics are measured as many times as the preset number of times of averaging (step S313—NO). In addition, a time of about 1 ms is required for the influence of the previous elastic surface wave to disappear, so that second and following measurements are conducted 1 ms or more after the previous measurement (step S314). That is, to again input a signal to the first fluid measurement device 30A after a signal has been input to the fluid measurement device 30A, the controller 121 judges whether 1 ms or more has passed since the previous input of the burst signal to the fluid measurement device 30A. If 1 ms or more has not passed (step S314—NO), the controller 121 waits for 1 ms or more. The controller 121 also judges whether the timing of inputting the high-frequency burst signal to each of the fluid measurement devices 30A to 30Y overlaps the detection timing in step S307. When the input timing overlaps the detection timing, the input timing is shifted to prevent from overlapping the detection timing (step S315). The procedure then moves to step S305.

After the processing in steps S305 to S315 is performed as many times as the number of times of averaging, average values of the measurement data in the fluid measurement devices 30A to 30Y are calculated by the corresponding averagers 118A to 118Y (steps S313—YES, S316). The average values of the measurement data calculated by the averagers 118A to 118Y are stored in the corresponding storages 119A to 119Y.

When the measurements by all of the fluid measurement devices 30A to 30Y are completed, the inflow gas valve ring 35 and the outflow gas valve ring 36 are rotated in each of the fluid measurement devices 30A to 30Y (step S321), and the procedure then moves to the measurement in the next fluid measurement section 2B1 (step S317—NO).

If the measurement time required for one gas measurement sensor 11 is $t_0$, the fluid measurement sections 2A1 to 2F1 into which the gas is introduced are sequentially switched every $t_0/6$ in, for example, the fluid measurement device 30A. Thus, the fluid measurement sections 2A1 to 2F1 to measure the gas are sequentially switched every $t_0/6$. If the number of times of averaging is 100, $t_0$ is 2.2 seconds.

Here, in order to continue the gas measurement, the second transmission switch 115 is switched to the fluid measurement sections 2A1 to 2F1 performing a next gas measurement (step S322). To obtain quantitatively accurate measurement results, there is a wait of a time $t_4$ which is required from the introduction of the gas into the gas measurement chambers 10 of the fluid measurement sections 2A1 to 2F1 performing the next gas measurement to the completion of the action of the gas on the sensitive film of the gas measurement sensor 11 (step S319). In step S319, a judgment may be made by whether the time interval $t_0$ necessary for the gas measurement has passed since the previous measurements in the fluid measurement sections 2A1 to 2F1 performing measurement. Moreover, in order to only obtain the relative difference or changes of the gases measured by the fluid measurement devices 30A to 30Y, it is not always necessary to wait for the time $t_4$ or $t_0$ to pass.

Furthermore, the operations in steps S319 to S322 are performed until the measurements are finished (step S317—NO).

The fluid spacial distribution visualization device 100 inputs a high-frequency burst signal to, for example, the first fluid measurement device 30A. In this case, before the detection time at which the output signal from the first fluid measurement device 30A is detected, the first transmission switch 112 sequentially switches the input destination of the high-frequency burst signal to the other fluid measurement devices 30B to 30Y. Further, after the first detection time, the response characteristics of the output signals of the first fluid measurement device 30A to the last fluid measurement device 30Y are sequentially detected. Thus, in measuring the response characteristics of the fluid measurement devices 30A to 30Y to which the high-frequency burst signal from the single set frequency generator 110 is input, the fluid spacial distribution visualization device 100 measures more rapidly than when measuring the response characteristics of one fluid measurement device 30 and then measuring the response characteristics of the other fluid measurement devices 30.

Furthermore, in the fluid spacial distribution visualization device 100, the measurement gas is sequentially introduced into the gas measurement chambers 10 of the fluid measurement sections 2A1 to 2F1 every $t_0/6$ in, for example, the fluid measurement device 30A, and measurements are sequentially conducted every $t_0/6$ in the fluid measurement sections 2A1 to 2F1. This applies to the fluid measurement devices 30B to 30Y. Thus, the time resolution of each measurement by the fluid measurement devices 30A to 30Y is $t_0/6$, and is not limited by the measurement time $t_0$ necessary for one gas measurement sensor 11. That is, the fluid measurement sections 2A1 to 2F1 in the fluid measurement devices 30A to 30Y cooperate in introducing a gas into the gas measurement chambers 10, and wait in parallel for the time in which the introduced gas acts on the sensitive films of the gas measurement sensors 11. Thus, the time resolution of each of the measurement by the fluid measurement devices 30A to 30Y can be increased without being limited by the gas measurement time $t_0$ necessary for one gas measurement sensor 11.

Figure 11:
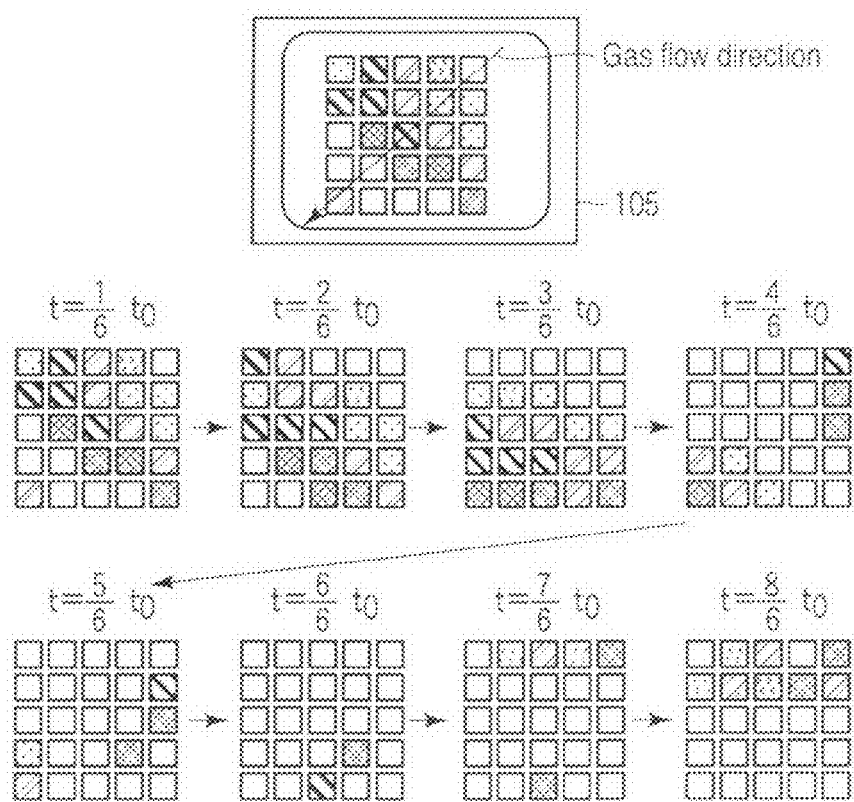
FIG. 11 is a schematic diagram showing, with time, gas distributions displayed on a display section of the fluid spacial distribution visualization device according to the fifth embodiment.

Therefore, in the fluid spacial distribution visualization device 100, the change of the hydrogen concentration measured by the fluid measurement devices 30A to 30Y can be updated every $t_0/6$ and displayed on the display unit 105 as shown in FIG. 11. Here, the change of the hydrogen concentration can be displayed every 0.37 seconds if $t_0$ is 2.2 seconds.

Consequently, the fluid spacial distribution visualization device 100 that uses the fluid measurement devices 30A to 30Y can make a response within a time shorter than one second. Thus, unevenness of the gas concentration can be visualized. For example, it can be observed in FIG. 11 that the unevenness of the hydrogen concentration runs in a direction indicated by an arrow, so that the presence of a source of hydrogen in a direction opposite to the arrow can be known.

Accordingly, the fluid spacial distribution visualization device 100 having the configuration described above has the following effects. That is, in the fluid spacial distribution visualization device 100, the high-frequency burst signal is input to, for example, the first fluid measurement device 30A. In this case, before the detection time at which the output signal from the first fluid measurement device 30A is detected, the first transmission switch 112 sequentially switches the input destination of the high-frequency burst signal to the other fluid measurement devices 30B to 30Y. Further, after the first detection time, the response characteristics of the output signals of the first fluid measurement device 30A to the last fluid measurement device 30Y are sequentially detected. Thus, in measuring the response characteristics of the fluid measurement devices 30A to 30Y to which the high-frequency signal from the single set frequency generator 110 is input, the fluid spacial distribution visualization device 100 can measure more rapidly than when measuring the response characteristics of one fluid measurement device 30 and then measuring the response characteristics of the other fluid measurement devices 30.

Furthermore, the fluid measurement sections 2A1 to 2F1 in the fluid measurement devices 30A to 30Y cooperate in introducing a gas into the gas measurement chambers 10, and wait in parallel for the time in which the introduced gas acts on the sensitive films of the gas measurement sensors 11. Thus, the time resolution of each of the measurement by the fluid measurement devices 30A to 30Y can be increased without being limited by the measurement time $t_0$ necessary for one gas measurement sensor 11. Consequently, the fluid spacial distribution visualization device 100 can make a response within a time shorter than one second and can visualize unevenness of the gas concentration.

Although measurement results by the fluid measurement devices 30A to 30Y are displayed by the depth of a color in the display screen 130 of the display unit 105, the kinds of colors can be changed and displayed as well. In this manner, not only the concentration of a particular fluid but also the kinds of fluids can be measured.

Sixth Embodiment

Now, a fluid spacial distribution visualization device 200 according to a sixth embodiment of the present invention is described with reference to FIG. 12 to FIG. 16. It should be noted that the same parts as those in the fifth embodiment (see FIG. 7 to FIG. 11) are provided with the same reference numbers and are not described.

Figure 12:
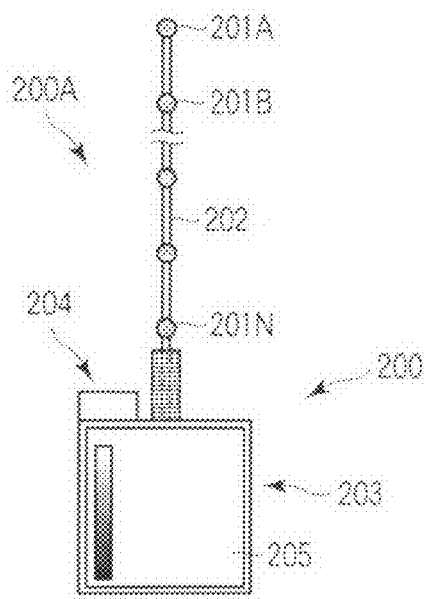
FIG. 12 is a front view showing the configuration of a fluid spacial distribution visualization device according to a sixth embodiment of the present invention.

FIG. 12 is a diagram showing the configuration of the fluid spacial distribution visualization device 200 according to the present embodiment. The fluid spacial distribution visualization device 200 includes a distribution measurement unit 200A and a display unit 203. The distribution measurement unit 200A includes a linear rod-like support (support pipe) 202 and a plurality of fluid measurement devices 201A to 201N. The fluid measurement devices 201A to 201N are supported on the linear rod-like support 202 a predetermined distance apart from one another (at regular intervals in the present embodiment). The proximal end of the support 202 is fixed to a predetermined position of an exterior housing of the display unit 203.

A position information measuring unit 204 is fixed to the exterior housing of the display unit 203. The display unit 203 includes a display 205 exposed in the outer surface of the exterior housing.

The position information measuring unit 204 includes at least one of an unshown known acceleration sensor and angular velocity sensor, and in the present embodiment, includes both of the known acceleration sensor and angular velocity sensor. The acceleration sensor and angular velocity sensor are capable of acting in at least two X-axis and Y-axis directions, and are preferably capable of acting in three directions including a Z-axis direction in addition to the above-mentioned two directions.

Figure 13:
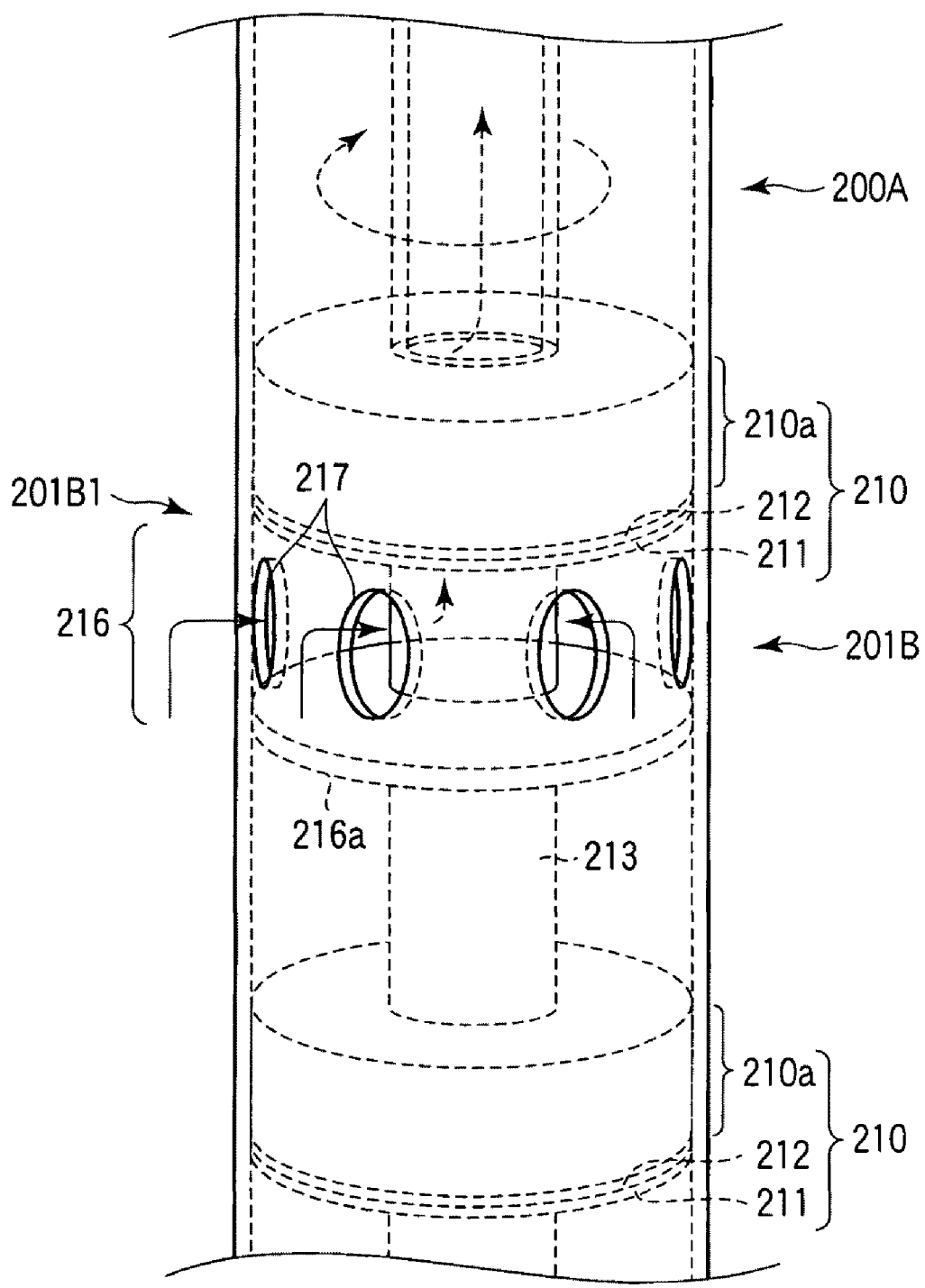
FIG. 13 is a perspective view showing the internal configuration of a support which supports a fluid measurement device of the fluid spacial distribution visualization device according to the sixth embodiment.
Figure 14:
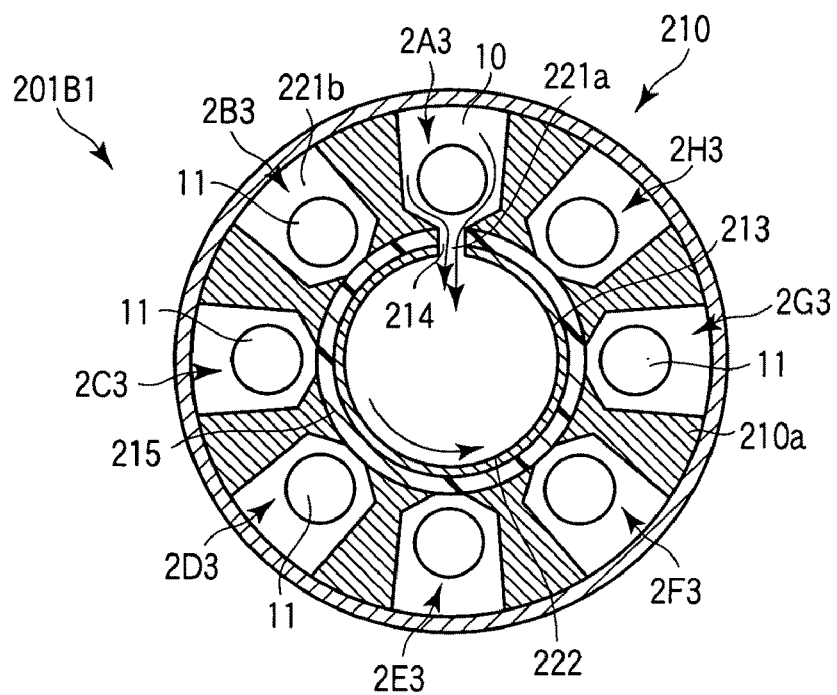
FIG. 14 is a sectional view showing the internal configuration of a sensor holder of the fluid measurement device of the fluid spacial distribution visualization device according to the sixth embodiment.
Figure 15:
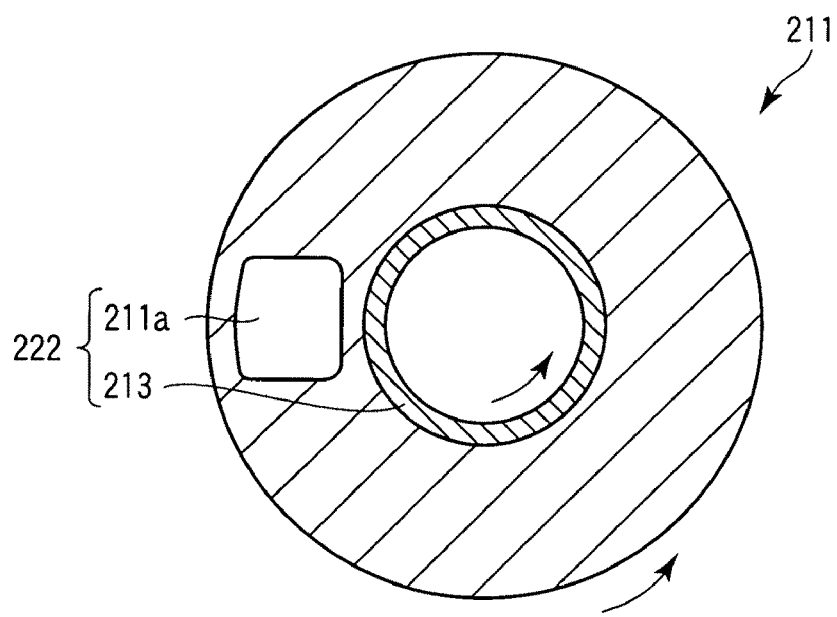
FIG. 15 is a sectional view showing the configuration of a gas valve ring of the fluid measurement device of the fluid spacial distribution visualization device according to the sixth embodiment.

The configuration of the distribution measurement unit 200A is described with reference to FIG. 13 to FIG. 15. FIG. 13 is an enlarged view of part of the support 202, and shows the configuration of the peripheral part of one of the fluid measurement devices 201A to 201N, for example, the fluid measurement device 201B. FIG. 14 is a diagram showing the internal configuration of the fluid measurement device 201B.

The fluid measurement device 201B includes a fluid measurement unit 201B1. The fluid measurement unit 201B1 includes a plurality of (eight in the present embodiment) fluid measurement sections 2A3 to 2H3. The fluid measurement sections 2A3 to 2H3 are concentrically provided in the fluid measurement unit 201B1. Here, the fluid measurement sections 2A3 to 2H3 have the same configuration. It should be noted that the configuration of one fluid measurement section 2A3 is only described below as an example and the same components of the other fluid measurement sections 2B3 to 2H3 are provided with the same reference numbers and are not described.

The fluid measurement unit 201B1 includes a cylindrical gas introduction pipe 216, a unit main body 210 and a rotary suction pipe 213. The unit main body 210 includes a sensor holder 210a, a metal mesh filter 212 and a gas valve ring 211. The gas measurement chambers 10 of the fluid measurement sections 2A3 to 2H3 are concentrically provided in the sensor holder 210a. A gas measurement sensor 11 which measures a gas as a specimen is provided in the gas measurement chamber 10 of each of the fluid measurement sections 2A3 to 2H3.

An outflow opening (outflow portion) 221a leading out of the gas measurement chamber 10 of each of the fluid measurement sections 2A3 to 2H3 is formed in the inner peripheral surface of the sensor holder 210a. Moreover, an inflow opening (inflow portion) 221b leading to the gas measurement chamber 10 of each of the fluid measurement sections 2A3 to 2H3 is formed in the bottom surface of the sensor holder 210a.

The gas introduction pipe 216 is disposed under the unit main body 210 in FIG. 13. A plurality of gas suction holes 217 are provided in the outer peripheral surface of the gas introduction pipe 216. The mesh filter 212 and the gas valve ring 211 are provided between the gas introduction pipe 216 and the unit main body 210. As shown in FIG. 15, the gas valve ring 211 is fixed to the rotary suction pipe 213, and is controlled by an unshown rotation controller (measurement controller) to rotate together with the rotary suction pipe 213.

A gas supply opening (movable inflow portion) 211a in communication with the inflow opening 221b of one of the fluid measurement sections 2A3 to 2H3 is formed in the gas valve ring 211. The mesh filter 212 is fixed to the gas valve ring 211 to cover the gas supply opening 211a. The mesh filter 212 does not necessarily have to be fixed to the gas valve ring 211 and may be fixed to the unit main body 210.

As shown in FIG. 14, the rotary suction pipe 213 is provided with a gas suction hole (movable outflow portion) 214 which can be in communication with the outflow opening 221a of one of the fluid measurement sections 2A3 to 2H3. An unshown suction unit is coupled to the rotary suction pipe 213.

The gas as a specimen is sucked into the gas introduction pipe 216 from the gas suction holes 217 of the gas introduction pipe 216 in FIG. 13 by suction force from the unshown suction unit. At the same time, the gas valve ring 211 and the rotary suction pipe 213 are rotated together by the rotation controller. Further, the gas within the gas introduction pipe 216 is sucked from the inflow opening 221b into the gas measurement chambers 10 of the fluid measurement sections 2A3 to 2H3 in communication with the gas supply opening 211a of the gas valve ring 211. At the same time, the gas suction hole 214 of the rotary suction pipe 213 is brought into communication with the outflow opening 221a of one of the fluid measurement sections 2A3 to 2H3, as shown in FIG. 14. That is, the inflow openings 221b of the fluid measurement sections 2A3 to 2H3 are sequentially switched and brought into communication with the gas supply opening 211a of the gas valve ring 211 by the combined rotation of the gas valve ring 211 and the rotary suction pipe 213. The outflow openings 221a of the fluid measurement sections 2A3 to 2H3 are also sequentially switched and brought into communication with the gas suction hole 214 of the rotary suction pipe 213. In this manner, a switch section 222 is formed to switch the flow of a measurement fluid into the gas measurement chamber 10 of each of the fluid measurement sections 2A3 to 2H3.

A gas leakage preventing grease 215 is applied to the outer peripheral surface of the rotary suction pipe 213. The grease 215 prevents the leakage of the gas from the gas measurement chamber 10 of each of the fluid measurement sections 2A3 to 2H3 during the measurement of the gas by the gas measurement sensor 11. Moreover, a suction pipe support plate 216a is provided within the support 202 and supports the rotary suction pipe 213.

Now, the action of the fluid spacial distribution visualization device 200 according to the present embodiment is described with reference to FIG. 16. To conduct a measurement, the fluid spacial distribution visualization device 200 is first held at a start position (initial position) to start a gas measurement in a desired space, as shown in the left part of FIG. 16. The fluid measurement devices 201A to 201N are then used to measure gas concentrations at positions where the fluid measurement devices 201A to 201N are arranged in the above-mentioned desired space.

Measurement values obtained by the fluid measurement devices 201A to 201N and position information (the initial position shown in the left part of FIG. 16) of the fluid measurement devices 201A to 201N measured by the position information measuring unit 204 at the end of the measurement of the gas concentration are input to the display unit 203 by the central control unit 104 (visualizer 122) described above in the fifth embodiment. On the basis of the measurement values of the gas concentrations by the fluid measurement devices 201A to 201N and position information of the fluid measurement devices 201A to 201N, a linear distribution D1 of the gas concentrations in the two-dimensional space at the initial position shown in the left part of FIG. 16 is displayed on the display section 205.

Figure 16:
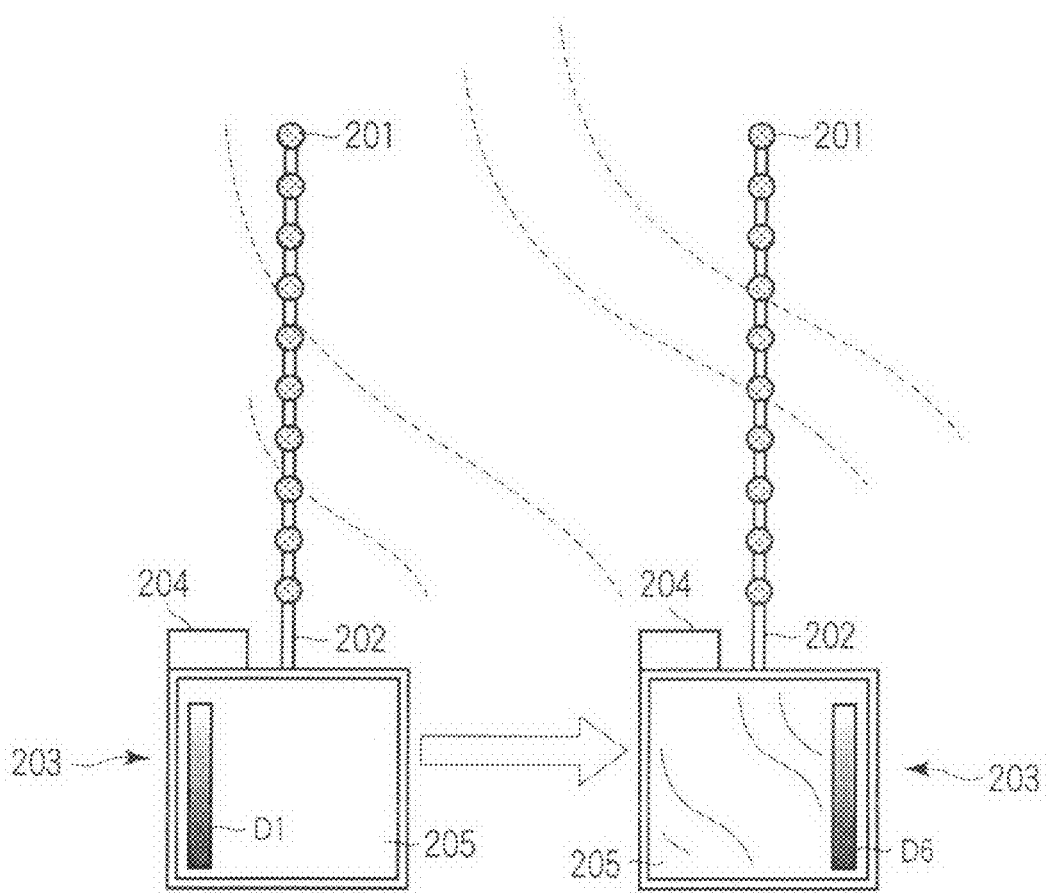
FIG. 16 is a schematic diagram illustrating the action of the fluid spacial distribution visualization device according to the sixth embodiment.

The fluid spacial distribution visualization device 200 is then horizontally and linearly moved to an end position indicated in the right part of FIG. 16 from the initial position shown in the left part of FIG. 16. Here, during the movement, each of the fluid measurement devices 201A to 201N conduct measurements not only at the initial position and the end position but also at, for example, four positions located at regular intervals between the initial position and the end position. In this case, the display unit 203 can display, on the display section 205, a linear distribution of the gas concentrations measured by each of the fluid measurement devices 201A to 201N whenever measurements are conducted at four places. The distribution of the gas concentrations at the above-mentioned four places is displayed on the display section 205, for example, in the same manner as the distribution D1 displayed on the display section 205 at the initial position shown in the left part of FIG. 16 or a distribution D6 displayed on the display section 205 at the end position indicated in the right part of FIG. 16.

Furthermore, rough distributions of the actual gas concentrations from the initial position to the end position are displayed on the display unit 203 on the basis of the linear distributions D1, . . . D6 of the gas concentrations measured by each of the fluid measurement devices 201A to 201N at a plurality of positions from the initial position to the end position. For example, suppose that there is actually a gas concentration distribution indicated by striped broken lines in a quadrangular horizontal space region (region in which the support 202 has moved) from the initial position shown in the left part of FIG. 16 to the end position indicated in the right part of FIG. 16. In this case, the actual gas concentration distribution is displayed as shown by striping in solid lines in the quadrangular region of the display section 205 of the display unit 203 of the fluid spacial distribution visualization device 200 at the end position indicated in the right part of FIG. 16.

In addition, the position of each of the fluid measurement devices 201A to 201N with reference to the initial position during the movement is also input to the display unit 203 in accordance with the information from the position information measuring unit 204.

The fluid spacial distribution visualization device 200 according to the present embodiment inputs a high-frequency burst signal to, for example, the first fluid measurement device 201A. In this case, as in the fifth embodiment, before a detection time at which an output signal from the first fluid measurement device 201A is detected, the first transmission switch 112 sequentially switches the input destination of the high-frequency burst signal to the other fluid measurement devices 201B to 201N. Further, after the first detection time, the response characteristics of the output signals of the first fluid measurement device 201A to the last fluid measurement device 201N are sequentially detected.

Furthermore, if the measurement time required for one gas measurement sensor 11 of each of the fluid measurement sections 2A3 to 2H3 of the first fluid measurement device 201A is, for example, $t_0$, the fluid measurement sections 2A3 to 2H3 in which a gas exchange is carried out by the gas supply opening 211a of the gas valve ring 211 and the gas suction hole 214 of the rotary suction pipe 213 are sequentially switched every $t_0/8$. As a result, a gas measurement operation is sequentially performed $t_0/8$ in each of the fluid measurement sections 2A3 to 2H3 of the first fluid measurement device 201A. This applies to the fluid measurement devices 201B to 201N. Thus, the time resolution of each of the measurement by the fluid measurement devices 201A to 201N is $t_0/8$.

Thus, if $t_0$ is 2.2 seconds as described above, a gas measurement is conducted every 0.28 seconds in each of the fluid measurement devices 201A to 201N. Thus, during the movement of the support 202, gas concentrations can be measured at more measurement positions in the quadrangular horizontal space region from the initial position shown in the left part of FIG. 16 to the end position indicated in the right part of FIG. 16. Moreover, a gas measurement can be conducted with a time resolution shorter than one second, so that unevenness of the gas concentration can be visualized.

Accordingly, the fluid spacial distribution visualization device 200 having the configuration described above has the following effects. That is, the fluid spacial distribution visualization device 200 inputs a high-frequency burst signal to, for example, the first fluid measurement device 201A. In this case, before the detection time at which an output signal from the first fluid measurement device 201A is detected, the first transmission switch 112 sequentially switches the input destination of the high-frequency burst signal to the other fluid measurement devices 201B to 201N. Further, after the first detection time, the response characteristics of the output signals of the first fluid measurement device 201A to the last fluid measurement device 201N are sequentially detected. Thus, in measuring the response characteristics of the fluid measurement devices 201A to 201N to which the high-frequency signal from the single set frequency generator 110 is input, the fluid spacial distribution visualization device 200 can measure more rapidly than when measuring the response characteristics of one fluid measurement device 201 and then measuring the response characteristics of the other fluid measurement devices 201.

Furthermore, the gas measurement chambers 10 of the fluid measurement sections 2A3 to 2H3 in the fluid measurement devices 201A to 201N cooperate in introducing a gas, and wait in parallel for the time in which the introduced gas acts on the sensitive films of the gas measurement sensors 11. Thus, the time resolution of each of the measurement by the fluid measurement devices 201A to 201N can be increased without being limited by the measurement time $t_0$ necessary for one gas measurement sensor 11. Consequently, the fluid spacial distribution visualization device 200 can make a response within a time shorter than one second and can visualize the flow of the gas.

(Modification)

According to the present invention, a fluid (gas or liquid) introduced to the inside is measured by the fluid measurement section. Thus, the fluid measurement section may modify or concentrate the fluid by a drug solution or by energy irradiation. Such a process or function may be included in the measurement operation in the fluid measurement section.

Furthermore, a function of separating or dissociating an adsorbate or reactant to initialize the sensitive film may be included in the measurement operation in the fluid measurement section. In general, the amount of target molecules is small in a gas measurement or in a measurement of a physiological substance, so that the sensitivity of the gas measurement sensor in the fluid measurement section needs to be enhanced. When the sensitive film is used in the gas measurement sensor, how the gas adheres to the sensitive film that changes with the equilibrium condition of the gas concentration within the gas measurement chamber 10 of the fluid measurement section may be measured. However, in this case, the gas that has once adhered to a sensitive film having high sensitivity is difficult to separate therefrom. If an irreversible sensitive film is used as the gas measurement sensor of the fluid measurement section and the sensitive film is initialized, a highly sensitive gas measurement sensor can be used in a measurement in the fluid measurement section.

Still further, the gas measurement sensor 11 according to the present invention does not necessarily have to include the sensitive film. For example, the condition of gas adsorption may change depending on the difference of surface molecular structures. Moreover, as in a gas density measurement, changes in the propagation rate of the elastic surface wave (phase change) or changes in damping factor (changes in strength with revolution) may be used to conduct a measurement without using the sensitive film.

Further yet, the sensitive film may not be configured to only react with a particular gas. At present, many gas measurement sensors include a plurality of sensitive films which vary from one another in reaction characteristics depending on a structural or physical characteristic difference. Thus, a gas reacts with the respective sensitive films in parallel, and reaction amounts in the respective sensitive films are analyzed in a comprehensive manner, so that a target gas is specified or identified. That is, it is only necessary that the assistance of the sensitive film permits the output of the gas measurement sensor 11 to change in accordance with the presence, concentration and kind of the gas within the gas measurement chamber 10 so that the gas can be identified and detected.

Therefore, according to the present invention, the gas measurement sensor 11 of each fluid measurement section does not have to be a single sensor. As described above, the gas measurement sensor 11 may be a sensor which includes a plurality of sensitive films different in reaction characteristics and which analyzes reactions from the respective sensitive films to derive a measurement result. Moreover, each of the fluid measurement sections may include a thermometer and pressure gage in addition to the sensor that reacts with a gas, and may be configured to display measurement results by the thermometer and pressure gage. Further, the fluid measurement device may include a velocity controller which controls the switching velocity in the operation of sequentially switching the fluid measurement sections measuring a fluid.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A fluid measurement device comprising:
   a fluid measurement unit which includes a plurality of fluid measurement sections configured to measure a measurement fluid introduced into a measurement chamber from the outside, each of the fluid measurement sections including a fluid measurement sensor on which the measurement fluid introduced into the measurement chamber acts;
   a measurement controller which sequentially introduces the measurement fluid into each of the fluid measurement sections every set time shorter than a fluid measurement time required for one of the fluid measurement sections to conduct one fluid measurement, the measurement controller measuring the fluid to provide a time difference for each of the fluid measurement sections; and
   a central controller which accumulates fluid measurement data from the fluid measurement sensors and rapidly measures a change of the external measurement fluid.

2. The fluid measurement device according to claim 1, wherein each of the fluid measurement sections of the fluid measurement unit includes an inflow portion which brings the measurement fluid into the measurement chamber, an outflow portion which brings the measurement fluid out of the measurement chamber, and a valve which is provided in at least one of the inflow portion and the outflow portion and which opens/closes a path of the measurement fluid; and
   the measurement controller includes a valve controller which switches the valve to an open or closed state to provide a time difference in the set time for each of the fluid measurement sections.

3. The fluid measurement device according to claim 2, further comprising a pump to bring the measurement fluid into the measurement chamber of the fluid measurement section in which the valve is open.

4. The fluid measurement device according to claim 1, wherein each of the fluid measurement sections of the fluid measurement unit includes an inflow portion which brings the measurement fluid into the measurement chamber, an outflow portion which brings the measurement fluid out of the measurement chamber, and a pump which is provided in at least one of the inflow portion and the outflow portion and which brings the measurement fluid into the measurement chamber when driven; and
   the measurement controller includes a pump controller which switches the driving state of the pump to provide a time difference in the set time for each of the fluid measurement sections.

5. The fluid measurement device according to claim 1, wherein the fluid measurement unit includes
   a unit main body in which the measurement chambers of the fluid measurement sections are concentrically arranged, each of the fluid measurement sections including an inflow portion which brings the measurement fluid into the measurement chamber, and an outflow portion which brings the measurement fluid out of the measurement chamber to a direction opposite to an inflow direction, and
   a switch section which switches the flow of the measurement fluid brought into the measurement chamber of each of the fluid measurement sections;
   the switch section includes
   an inflow rotary disk which is disposed on the inflow direction side of the unit main body when facing the unit main body, the inflow rotary disk being rotatable with respect to the unit main body around a rotating axis extending through the axial center of the unit main body, the inflow rotary disk including a movable inflow portion which is brought into communication with the inflow portion of one of the fluid measurement sections during the rotation of the inflow rotary disk, and an outflow rotary disk which is disposed on an outflow direction side of the unit main body when facing the unit main body, the outflow rotary disk being rotatable together with the inflow rotary disk with respect to the unit main body around the rotating axis, the outflow rotary disk including a movable outflow portion that is brought into communication with the outflow portion of the fluid measurement section in which the movable inflow portion is in communication with the inflow portion during the rotation of the outflow rotary disk; and the measurement controller includes a rotation controller, the rotation controller rotating and driving the inflow rotary disk and the outflow rotary disk and switching the introduction of the measurement fluid to provide a time difference in the set time for each of the fluid measurement sections.

6. The fluid measurement device according to claim 1, wherein the fluid measurement unit includes a ring-shaped unit main body in which the measurement chambers of the fluid measurement sections are concentrically arranged, each of the fluid measurement sections including an inflow portion which brings the measurement fluid into the measurement chamber from an inner peripheral direction of the unit main body, and an outflow portion which brings the measurement fluid out of the measurement chamber to a direction different from an inflow direction, and a switch section which switches the flow of the measurement fluid brought into the measurement chamber of each of the fluid measurement sections;

the switch section includes a fluid supply cylinder which is disposed on the inner peripheral side of the unit main body when facing the unit main body, the fluid supply cylinder being rotatable with respect to the unit main body around a rotating axis extending through the axial center of the unit main body, the fluid supply cylinder including a movable inflow portion which is brought into communication with the inflow portion of one of the fluid measurement sections during the rotation of the fluid supply cylinder; and the measurement controller includes a rotation controller, the rotation controller rotating and driving the fluid supply cylinder and switching the introduction of the measurement fluid into the fluid measurement section to provide a time difference in the set time for each of the fluid measurement sections.

7. The fluid measurement device according to claim 1, wherein the fluid measurement unit includes a ring-shaped unit main body in which the measurement chambers of the fluid measurement sections are concentrically arranged, each of the fluid measurement sections including an outflow portion which brings the measurement fluid out of the measurement chamber to an inner peripheral direction of the unit main body, and an inflow portion which brings the measurement fluid into the measurement chamber from a direction different from an outflow direction, and a switch section which switches the flow of the measurement fluid brought out of the measurement chamber of each of the fluid measurement sections;

the switch section includes a fluid supply cylinder which is disposed on the inner peripheral side of the unit main body when facing the unit main body, the fluid supply cylinder being rotatable with respect to the unit main body around a rotating axis extending through the axial center of the unit main body, the fluid supply cylinder including a movable outflow portion which is brought into communication with the outflow portion of one of the fluid measurement sections during the rotation of the fluid supply cylinder; and the measurement controller includes a rotation controller, the rotation controller rotating and driving the fluid supply cylinder and switching the introduction of the measurement fluid into the fluid measurement section to provide a time difference in the set time for each of the fluid measurement sections.

8. The fluid measurement device according to claim 1, wherein the fluid measurement sensors are gas sensors on which a gas serving as the measurement fluid acts.

9. The fluid measurement device according to claim 8, wherein each of the gas sensors includes a plurality of sensor elements, each of the sensor elements includes a sensitive film having gas response characteristics different from those of the other sensor elements, and the central controller calculates an output from each of the gas sensor elements, and measures at least one of the kind and concentration of the measurement fluid.

10. The fluid measurement device according to claim 9, wherein the gas sensors are spherical elastic surface wave element sensors, and each of the spherical elastic surface wave element sensors is made of a substance which changes in elastic properties in response to the action of the measurement fluid.

11. The fluid measurement device according to claim 9, wherein the gas sensors are spherical elastic surface wave element sensors, and each of the spherical elastic surface wave element sensors includes the sensitive film which adsorbs a predetermined component contained in the measurement fluid.

12. The fluid measurement device according to claim 9, wherein the gas sensors are electric resistance gas sensors, each of the electric resistance gas sensors includes the sensitive film which adsorbs the measurement fluid and thereby changes in electric resistance, and the central controller measures the electric resistance of the sensitive film and thereby measures a change of the measurement fluid.

13. The fluid measurement device according to claim 9, wherein the gas sensors are field effect transistor type gas sensors, each of the field effect transistor type gas sensors includes the sensitive film which adsorbs the measurement fluid and thereby changes in work function, and the central controller measures a threshold voltage and resistance change of the sensitive film and thereby calculates the work function and measures a change of the measurement fluid.

14. A method of measuring a fluid, the method comprising:
measuring the fluid in a plurality of fluid measurement sections in which fluid measurement sensors are respectively disposed in measurement chambers, the measurement of the fluid being conducted by sequentially introducing the measurement fluid into each of the fluid measurement sections every set time shorter than a fluid measurement time required for one of the fluid measurement sections to conduct one fluid measurement and causing the measurement fluid to act on the fluid measurement sensors to provide a time difference for each of the fluid measurement sections; and accumulating fluid measurement data from the fluid measurement sensors and rapidly measuring a change of the external measurement fluid.

15. A fluid spacial distribution visualization device comprising:

a plurality of fluid measurement devices which respectively measure a change of a predetermined measurement fluid at different positions, each of the fluid measurement devices including a plurality of fluid measurement sections configured to measure the measurement fluid introduced into a measurement chamber from the outside, each of the fluid measurement sections including a fluid measurement sensor on which the measurement fluid introduced into the measurement chamber acts;

a display unit which displays a distribution of the measurement fluid in a space of two or more dimensions on the basis of a measurement value of the measurement fluid measured by each of the fluid measurement devices;

a measurement control unit which sequentially introduces the measurement fluid into each of the fluid measurement sections every set time shorter than a fluid measurement time required for one of the fluid measurement sections to conduct one fluid measurement in each of the fluid measurement devices, the measurement control unit measuring the fluid to provide a time difference for each of the fluid measurement sections in each of the fluid measurement devices; and a central control unit which accumulates fluid measurement data from the fluid measurement sensors in each of the fluid measurement devices and rapidly measures a change of the external measurement fluid in each of the fluid measurement devices, the central control unit including a visualizer configured to visualize and display, on the display unit, the change of the measurement fluid obtained from the fluid measurement data in each of the fluid measurement devices.

16. The fluid spacial distribution visualization device according to claim 15, wherein the display unit includes display elements, the number of the display elements provided being the same as the number of fluid measurement devices, and the visualizer detects one of the display element arranged at position corresponding to each of the fluid measurement devices in the display unit, and displays measurement result of the measurement fluid by each of the fluid measurement devices on the display element arranged at the corresponding position.

17. The fluid spacial distribution visualization device according to claim 15, further comprising:

a rod-like support pipe which supports the fluid measurement devices; and a position information measuring unit which measures position information of each of the fluid measurement devices, wherein the visualizer displays, on the display unit, the distribution of the measurement fluid in the space of two or more dimensions on the basis of the measurement value of the measurement fluid measured by each of the fluid measurement devices and on the basis of the position information of each of the fluid measurement devices measured by the position information measuring unit at the end of the measurement.

* * * * *